United States Patent
Nakayama

(10) Patent No.: US 12,023,183 B2
(45) Date of Patent: Jul. 2, 2024

(54) RADIOGRAPHY SYSTEM, IMAGE PROCESSING DEVICE, IMAGE PROCESSING METHOD, AND IMAGE PROCESSING PROGRAM

(71) Applicant: FUJIFILM CORPORATION, Tokyo (JP)

(72) Inventor: Hiroki Nakayama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 184 days.

(21) Appl. No.: 17/591,612

(22) Filed: Feb. 3, 2022

(65) Prior Publication Data
US 2022/0273250 A1 Sep. 1, 2022

(30) Foreign Application Priority Data
Feb. 26, 2021 (JP) .................. 2021-031247

(51) Int. Cl.
| | |
|---|---|
| A61B 6/02 | (2006.01) |
| A61B 6/00 | (2006.01) |
| A61B 6/06 | (2006.01) |
| A61B 6/40 | (2024.01) |
| A61B 6/46 | (2024.01) |
| A61B 6/50 | (2024.01) |

(Continued)

(52) U.S. Cl.
CPC .............. *A61B 6/025* (2013.01); *A61B 6/06* (2013.01); *A61B 6/4007* (2013.01); *A61B 6/463* (2013.01); *A61B 6/465* (2013.01); *A61B 6/502* (2013.01); *A61B 6/5205* (2013.01); *A61B 6/587* (2013.01); *G06T 7/74* (2017.01); *G06T 11/005* (2013.01)

(58) Field of Classification Search
None
See application file for complete search history.

(56) References Cited

U.S. PATENT DOCUMENTS

| | | | |
|---|---|---|---|
| 6,206,566 B1 | 3/2001 | Schuetz | |
| 8,804,912 B2 * | 8/2014 | Akahori | A61B 6/025 378/165 |

(Continued)

FOREIGN PATENT DOCUMENTS

| | | |
|---|---|---|
| EP | 2730226 A1 | 5/2014 |
| JP | 2010183965 A | 8/2010 |

(Continued)

OTHER PUBLICATIONS

English translation of JP 2011-183004 A (Year: 2011).*

(Continued)

*Primary Examiner* — Thomas R Artman
(74) *Attorney, Agent, or Firm* — SOLARIS Intellectual Property Group, PLLC

(57) ABSTRACT

A radiography system includes a correction marker that is used to obtain a marker image included in at least one of a plurality of projection images obtained by tomosynthesis imaging, is provided in an irradiation path of radiation in a radiation emitting unit, and is disposed at the position where the marker image is included in a region other than a reconstructed region in the projection image, the reconstructed region being a region used in a case in which the tomographic image is reconstructed from the plurality of projection images among the regions included in the plurality of projection images.

16 Claims, 15 Drawing Sheets

(51) Int. Cl.
*A61B 6/58* (2024.01)
*G06T 7/73* (2017.01)
*G06T 11/00* (2006.01)

(56) References Cited

U.S. PATENT DOCUMENTS

| | | | |
|---|---|---|---|
| 9,380,985 B2* | 7/2016 | Akahori | A61B 6/587 |
| 11,179,126 B2* | 11/2021 | Sato | A61B 6/5205 |
| 11,266,369 B2* | 3/2022 | Inoue | A61B 6/545 |
| 2010/0252740 A1 | 10/2010 | Akahori et al. | |
| 2012/0014498 A1 | 1/2012 | Akahori | |
| 2014/0119500 A1* | 5/2014 | Akahori | A61B 6/584 |
| | | | 378/17 |
| 2017/0000451 A1 | 1/2017 | Aspelund et al. | |
| 2020/0046311 A1 | 2/2020 | Vogelsang et al. | |
| 2020/0100746 A1* | 4/2020 | Sato | A61B 6/027 |
| 2020/0275902 A1* | 9/2020 | Inoue | A61B 6/0435 |
| 2022/0273249 A1* | 9/2022 | Nakayama | A61B 6/4007 |
| 2022/0273250 A1* | 9/2022 | Nakayama | A61B 6/502 |

FOREIGN PATENT DOCUMENTS

| | | |
|---|---|---|
| JP | 2011183004 A | 9/2011 |
| JP | 2011188972 A | 9/2011 |
| JP | 2012-020023 A | 2/2012 |
| JP | 2017-500921 A | 1/2017 |

OTHER PUBLICATIONS

Extended European Search Report dated Jul. 15, 2022, issued in corresponding EP Patent Application No. 22154955.3.

English language translation of the following: Office action dated May 14, 2024, from the JPO in a Japanese patent application No. 2021-031247 corresponding to the instant patent application. This office action translation is submitted now in order to supplement the understanding of the cited references which are being disclosed in the instant Information Disclosure Statement.

* cited by examiner

RADIOGRAPHY SYSTEM, IMAGE PROCESSING DEVICE, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-031247 filed on Feb. 26, 2021. The above application is hereby expressly incorporated by reference, in its entirety, into the present application.

BACKGROUND

1. Technical Field

The present disclosure relates to a radiography system, an image processing device, an image processing method, and an image processing program.

2. Description of the Related Art

In general, so-called tomosynthesis imaging is known which includes a radiation tube generating radiation and irradiates an object with the radiation at each of a plurality of irradiation positions having different irradiation angles to capture a plurality of projection images of the object at different irradiation positions. In addition, in the tomosynthesis imaging, the plurality of projection images are reconstructed to generate a plurality of tomographic images.

In a case in which the plurality of projection images are reconstructed, it is necessary to calculate the position of the focus of the radiation tube in the capture of each projection image. It is necessary to know the position of the focus of the radiation tube as accurately as possible in order to perform the reconstruction accurately. However, the position of the focus of the radiation tube changes over time due to, for example, the deterioration and deformation of mechanical parts. JP2012-020023A discloses a technique in which a correction marker is provided on an imaging table or an object so as to be included in a projection image together with the object and the positional deviation amount of a focus indicating how much the position of the focus of a radiation tube deviates from a design value is derived from a marker image of the correction marker included in the projection image.

SUMMARY

In the above-mentioned technique according to the related art, since the correction marker is superimposed on the object in the projection image, the correction marker may be included in an object region of a tomographic image obtained by reconstructing a plurality of projection images.

The present disclosure has been made in view of the above circumstances, and an object of the present disclosure is to provide a radiography system, an image processing device, an image processing method, and an image processing program that can prevent an image of a correction marker from being included in a reconstructed region of a tomographic image obtained by reconstructing a plurality of projection images.

In order to achieve the above object, according to a first aspect of the present disclosure, there is provided a radiography system comprising: a radiation emitting unit including a radiation tube that generates radiation from a focus and an irradiation field limiter that is provided so as to correspond to the radiation tube and limits an irradiation field of the radiation; a radiation detector that receives the radiation, which has been emitted from the radiation emitting unit and transmitted through an object, to detect a projection image of the object; an imaging control device that irradiates the object with the radiation at a plurality of irradiation positions having different irradiation angles and controls tomosynthesis imaging; and a correction marker that is used to obtain a marker image included in at least one of a plurality of the projection images obtained by the tomosynthesis imaging, is provided in an irradiation path of the radiation in the radiation emitting unit, and is disposed at a position where the marker image is included in a region other than a reconstructed region in the projection image, the reconstructed region being a region used in a case in which the tomographic image is reconstructed from the plurality of projection images among regions included in the plurality of projection images.

According to a second aspect of the present disclosure, in the radiography system according to the first aspect, the correction marker may be disposed in the irradiation path of the radiation emitted at two irradiation positions which correspond to both ends of an irradiation angle range among the plurality of irradiation positions.

According to a third aspect of the present disclosure, in the radiography system according to the first aspect or the second aspect, the tomosynthesis imaging may be possible in a first irradiation angle range wider than an overall imaging irradiation angle range which is an irradiation angle range in which an entire tomographic image including an entire object is obtainable in a case in which the tomographic image is reconstructed from the projection images obtained at each of the plurality of irradiation positions, and the correction marker may be disposed in the irradiation path of the radiation emitted at an outer irradiation position which is outside the overall imaging irradiation angle range in the first irradiation angle range and where a partial tomographic image including only a part of the object is obtained.

According to a fourth aspect of the present disclosure, in the radiography system according to the third aspect, the radiation emitting unit may include a plurality of the radiation tubes.

According to a fifth aspect of the present disclosure, in the radiography system according to the fourth aspect, the correction marker may be provided in at least one of the irradiation field limiters which are provided so as to correspond to the radiation tubes disposed at the outer irradiation positions.

According to a sixth aspect of the present disclosure, in the radiography system according to any one of the third to fifth aspects, the radiation emitting unit may be movable to the plurality of irradiation positions.

According to a seventh aspect of the present disclosure, in the radiography system according to the sixth aspect, the correction marker may be moved into the irradiation path in a case in which the radiation emitting unit is located at least at the outer irradiation position and may be movable out of the irradiation path in a case in which the radiation emitting unit is located at the irradiation position other than the outer irradiation position.

According to an eighth aspect of the present disclosure, the radiography system according to any one of the first to seventh aspects may further comprise an image processing device that reconstructs the tomographic image using the plurality of projection images.

According to a ninth aspect of the present disclosure, in the radiography system according to any one of the first to eighth aspects, the correction marker may include a first correction marker that detects a deviation of a position of the focus in a left-right direction and a second correction marker that detects a deviation of the position of the focus in a direction intersecting the left-right direction.

Further, in order to achieve the above object, according to a tenth aspect of the present disclosure, there is provided an image processing device comprising at least one processor. The processor acquires a plurality of projection images obtained by tomosynthesis imaging from the radiography system according to the present disclosure and derives a positional deviation amount of a focus of a radiation tube used for the tomosynthesis imaging on the basis of a position of a marker image included in the projection image and a reference position of the marker image.

According to an eleventh aspect of the present disclosure, in the image processing device according to the tenth aspect, a tomographic image may be reconstructed from the plurality of projection images on the basis of the positional deviation amount.

Furthermore, in order to achieve the above object, according to a twelfth aspect of the present disclosure, there is provided an image processing device comprising at least one processor. The processor acquires a plurality of projection images obtained by tomosynthesis imaging from the radiography system according to the present disclosure and reconstructs a tomographic image from the plurality of projection images on the basis of a position of a marker image included in the projection image and a reference position of the marker image.

According to a thirteenth aspect of the present disclosure, in the image processing device according to the eleventh aspect or the twelfth aspect, the processor may reconstruct a plurality of first tomographic images, in which a part of the object is included, from a plurality of projection images including a projection image obtained by projection at an irradiation position outside an overall imaging irradiation angle range among the plurality of projection images and may reconstruct a plurality of second tomographic images, in which the entire object is included, from a plurality of projection images obtained by projection at irradiation positions inside the overall imaging irradiation angle range among the plurality of projection images. The overall imaging irradiation angle range may be an irradiation angle range in which an entire tomographic image including the entire object is obtainable in a case in which the tomographic image is reconstructed from the projection images obtained at each of the plurality of irradiation positions.

Moreover, in order to achieve the above object, according to a fourteenth aspect of the present disclosure, there is provided an image processing method executed by a computer. The image processing method comprises: acquiring a plurality of projection images obtained by tomosynthesis imaging from the radiography system according to the present disclosure; and deriving a positional deviation amount of a focus of a radiation tube used for the tomosynthesis imaging on the basis of a position of a marker image included in a projection image which is included in the acquired plurality of projection images and a reference position of the marker image.

In addition, in order to achieve the above object, according to a fifteenth aspect of the present disclosure, there is provided an image processing method executed by a computer. The image processing method comprising: acquiring a plurality of projection images obtained by tomosynthesis imaging from the radiography system according to the present disclosure; and reconstructing a tomographic image from the plurality of projection images on the basis of a position of a marker image included in a projection image which is included in the acquired plurality of projection images and a reference position of the marker image.

Further, in order to achieve the above object, according to a sixteenth aspect of the present disclosure, there is provided an image processing program that causes a computer to perform a process including: acquiring a plurality of projection images obtained by tomosynthesis imaging from the radiography system according to the present disclosure; and deriving a positional deviation amount of a focus of a radiation tube used for the tomosynthesis imaging on the basis of a position of a marker image included in a projection image which is included in the acquired plurality of projection images and a reference position of the marker image.

Furthermore, in order to achieve the above object, according to a seventeenth aspect of the present disclosure, there is provided an image processing program that causes a computer to perform a process including: acquiring a plurality of projection images obtained by tomosynthesis imaging from the radiography system according to the present disclosure; and reconstructing a tomographic image from the plurality of projection images on the basis of a position of a marker image included in a projection image which is included in the acquired plurality of projection images and a reference position of the marker image.

According to the present disclosure, it is possible to prevent the image of the correction marker from being included in the reconstructed region of the tomographic image obtained by reconstructing a plurality of projection images.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In addition, this embodiment does not limit the present disclosure.

Figure 1:
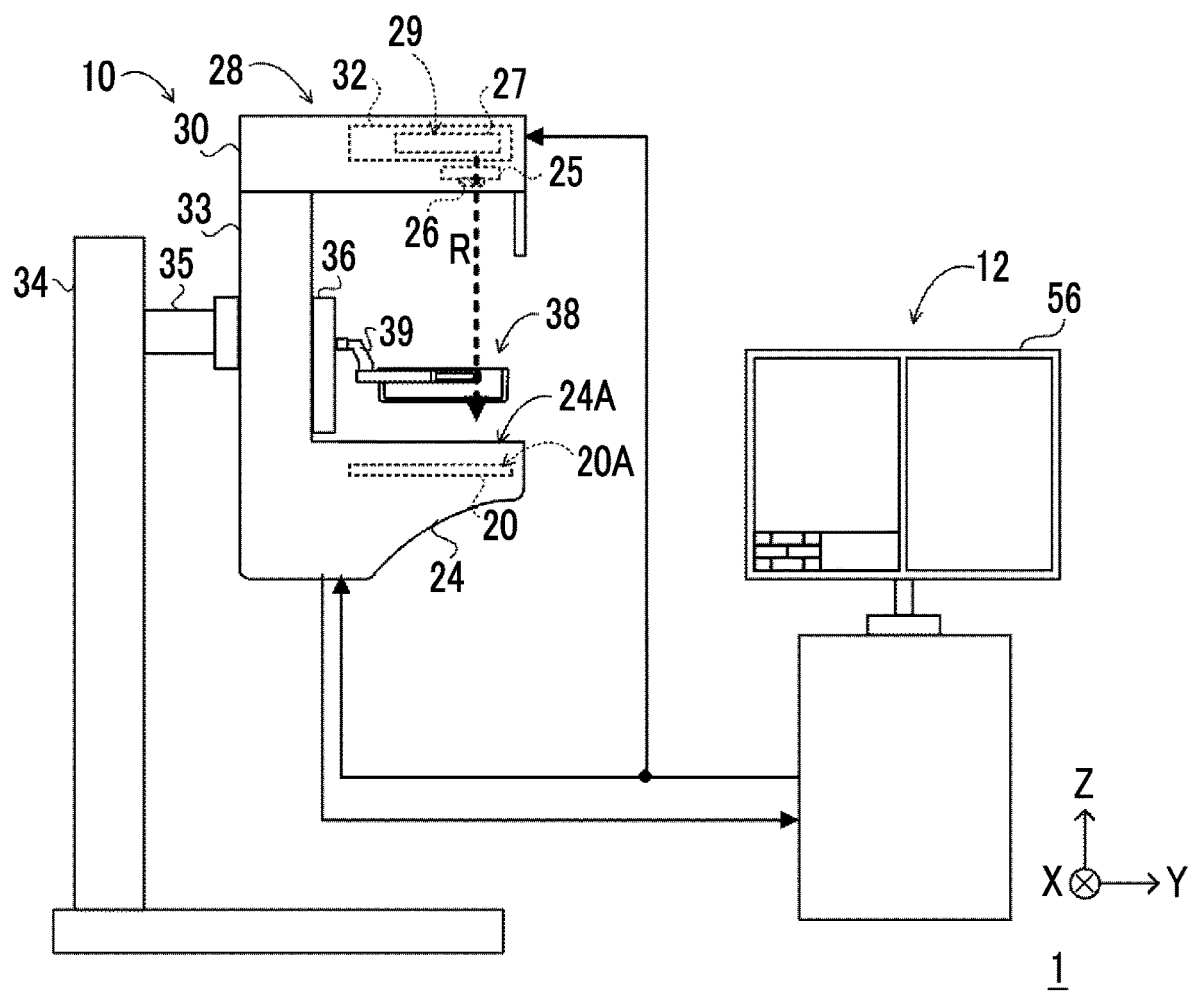
FIG. 1 is a diagram schematically illustrating an example of the overall configuration of a radiography system according to an embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from the left side of a subject. Further, the mammography apparatus 10 according to this embodiment is an example of an imaging control device according to the present disclosure.

The mammography apparatus 10 according to this embodiment is an apparatus that is operated under the control of the console 12 and irradiates the breast of the subject as an object with radiation R (for example, X-rays) to capture a radiographic image of the breast. In addition, the mammography apparatus 10 may be an apparatus that images the breast of the subject not only in a state in which the subject is standing (standing state) but also in a state in which the subject is sitting on, for example, a chair (including a wheelchair) (sitting state).

A radiation detector 20 detects the radiation R transmitted through the breast which is the object. Specifically, the radiation detector 20 detects the radiation R that has entered the breast of the subject and an imaging table 24 and reached a detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 that is used to compress the breast in a case in which imaging is performed is attached to a compression unit 36 that is provided in an arm portion 33. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24. The compression plate 38 according to this embodiment is an example of a compression member according to the present disclosure.

As illustrated in FIG. 1, the mammography apparatus 10 according to this embodiment comprises the imaging table 24, a radiation emitting unit 28, the arm portion 33, a base 34, and a shaft portion 35. The arm portion 33 is held by the base 34 so as to be movable in the up-down direction (Z-axis direction). Therefore, the height of the arm portion 33 can be adjusted according to the position of the breast of the subject. Further, a radiation source accommodation portion 30 that accommodates the radiation source 29 of the radiation emitting unit 28 is disposed in the arm portion 33. The radiation source accommodation portion 30 is supported integrally with the imaging table 24 by the arm portion 33. The arm portion 33 can be displaced with respect to the base 34 while maintaining a relative positional relationship between the radiation source 29 of the radiation emitting unit 28 and the radiation detector 20.

Figure 2:
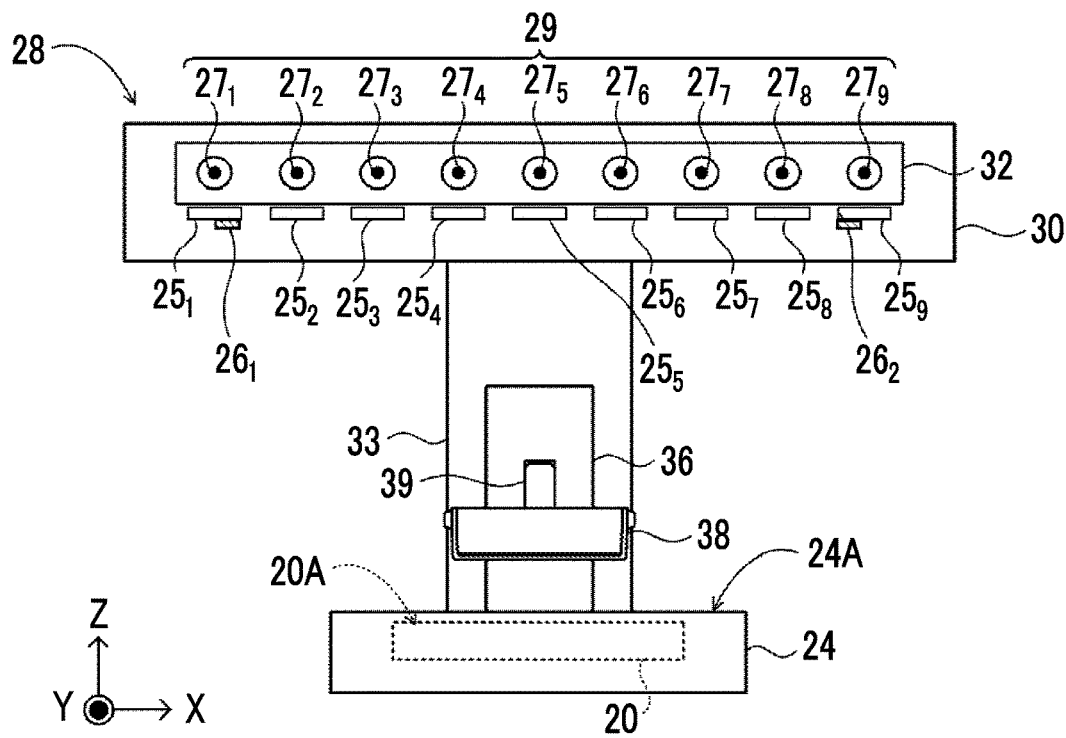
FIG. 2 is an example of a front view of a radiation emitting unit according to the embodiment as viewed from a subject.

FIG. 2 illustrates an example of a front view of the radiation emitting unit 28 according to this embodiment as viewed from the subject side. In addition, in FIG. 2, the base 34 is not illustrated. Further, FIG. 3 is a perspective view illustrating an example of the radiation source 29 accommodated in the radiation source accommodation portion 30.

Figure 3:
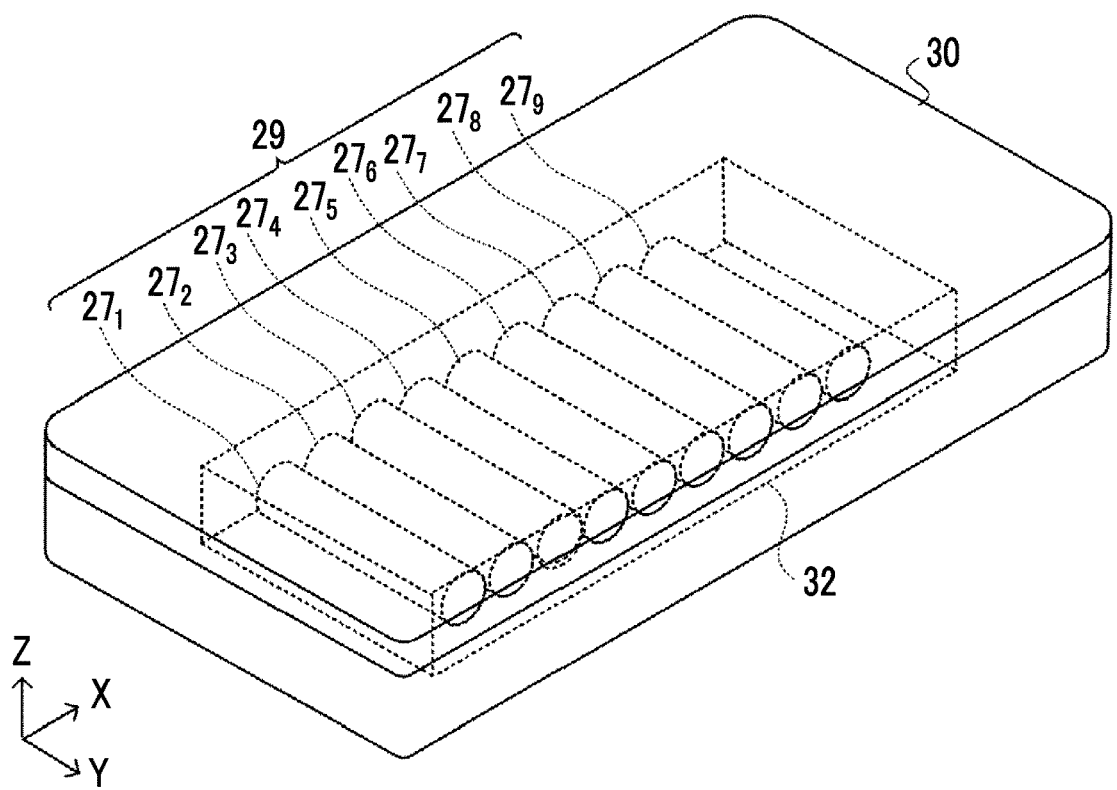
FIG. 3 is a perspective view illustrating an example of a radiation source accommodated in a radiation source accommodation portion.

As illustrated in FIGS. 2 and 3, the radiation emitting unit 28 includes a radiation source 29 having a plurality of radiation tubes $27_1$ to $27_j$ (j=2, 3, . . . , the maximum value is 9 in FIGS. 2 and 3) that emit the radiation R from the focus and collimators $25_1$ to $25_j$ (j=2, 3, . . . , the maximum value is 9 in FIGS. 2 and 3) that are provided so as to correspond to the radiation tubes 27 and limit the irradiation field of the radiation R. The radiation source 29 selectively emits the radiation R from each of the plurality of radiation tubes 27 to the object. In addition, the number of radiation tubes 27 and collimators 25 included in the radiation source 29 is not limited to this embodiment. Further, in this embodiment, in a case in which the radiation tubes $27_1$ to $27_9$ and the collimators $25_1$ to $25_9$ are generically referred to without being distinguished from each other, reference numerals "1 to 9" indicating the components are omitted, and the radiation tubes $27_1$ to $27_9$ and the collimators $25_1$ to $25_9$ are referred to as "radiation tubes 27" and "collimators 25", respectively.

As illustrated in FIGS. 2 and 3, the plurality of radiation tubes 27 are accommodated in a housing 32 and are accommodated in the radiation source accommodation portion 30 in a state of being arranged in one row in the X-axis direction. Here, the one row means an arrangement state in a plan view of the plurality of radiation tubes 27 as viewed from the Z-axis direction orthogonal to the detection surface 20A of the radiation detector 20. Further, as illustrated in FIG. 2, the radiation tubes 27 are disposed at irradiation positions where the radiation R is incident on the detection surface 20A of the radiation detector 20 at different angles.

The radiation tube 27 according to this embodiment has, for example, a cathode of a cold cathode type and an anode of a fixed anode type (which are not illustrated). Specifically, the cathode is a field-emission-type cathode that emits an electron beam using a field emission phenomenon that occurs in a case in which an electric field is applied to a surface of a conductor. Further, the anode is a target with which the electron emitted from the cathode collides and does not have a rotation structure in which a disk-shaped anode is rotated as in a rotating anode type.

Furthermore, the collimator 25 is provided for each radiation tube 27 and has a function of limiting the irradiation field of the radiation R emitted from the corresponding radiation tube 27. The collimator 25 according to this embodiment is an example of an irradiation field limiter according to the present disclosure.

Figure 4:
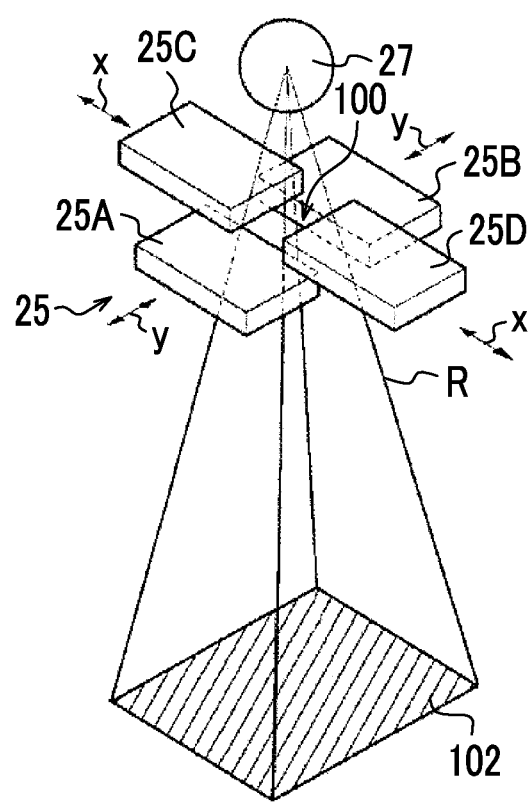
FIG. 4 is a perspective view illustrating an example of the configuration of a collimator according to the embodiment.

As illustrated in FIG. 2, the collimator 25 is provided between the radiation tube 27 and the imaging table 24. FIG. 4 is a perspective view illustrating an example of the configuration of the collimator 25 according to this embodiment. As illustrated in FIG. 4, for example, the collimator 25 according to this embodiment includes four blades 25A, 25B, 25C, and 25D. Each of the blades 25A to 25D is a plate-shaped member which has a rectangular shape in a plan view and is made of a material, such as lead or tungsten, that blocks the radiation R. In the collimator 25, one side surface of the blade 25A faces one side surface of the blade 25B, and one side surface of the blade 25C faces one side surface of the blade 25D. Further, in the collimator 25, an opening portion 100 that has a rectangular shape in a plan view is formed by the side surfaces of the blades 25A to 25D which face each other.

Each of the blades 25A to 25D is moved by a driving unit (not illustrated) including, for example, a motor. The blade 25A and the blade 25B can be moved in the y direction of FIG. 4, and the blade 25C and the blade 25D can be moved in the x direction of FIG. 4 which intersects the y direction. Further, in the collimator 25 according to this embodiment, the movable range of the blades 25A to 25D is a range from a state in which the leading ends of the blades facing each other come into contact with each other, that is, a state in which the opening portion 100 is fully closed to a state in which the opening portion 100 keeps a rectangular shape in a plan view and has the maximum area. The irradiation field 102 has a shape and size (area) corresponding to the shape and size (area) of the opening portion 100.

Further, the radiation source 29 according to this embodiment is provided with correction markers $26_1$ and $26_2$ corresponding to the radiation tubes $27_1$ and $27_9$. The correction markers $26_1$ and $26_2$ will be described in detail below.

In the mammography apparatus 10 according to this embodiment, for the capture of radiographic images, cranio-caudal (CC) imaging in which an imaging direction is a cranio-caudal direction, medio-lateral oblique (MLO) imaging in which an imaging direction is a medio-lateral oblique direction, and tomosynthesis imaging can be performed on the breast.

In a case in which the CC imaging is performed, the imaging surface 24A is adjusted to a state in which the imaging surface 24A faces the upper side of the mammography apparatus 10 (the head of the subject). Further, the position of the radiation tube 27 of the radiation source 29 is adjusted to the irradiation position facing the imaging surface 24A of the imaging table 24. Therefore, the radiation R is emitted from the radiation tube 27 to the breast in a direction from the head to the foot of the subject, and the CC imaging is performed.

In contrast, in a case in which the MLO imaging is performed, the position of the imaging table 24 is adjusted to a state in which the imaging surface 24A is rotated up to a predetermined angle in a range of, for example, 45 degrees or more and less than 90 degrees with respect to the case in which the CC imaging is performed. Specifically, in a case in which an image of the left breast is captured, the imaging surface 24A is inclined to the right. In a case in which an image of the right breast is captured, the imaging surface 24A is inclined to the left. Therefore, the radiation R is emitted from the radiation tube 27 to the breast in a direction from the center of the body of the subject to the outside (in a direction from a space between the breasts of the subject to the arm), and the MLO imaging is performed.

Figure 5:
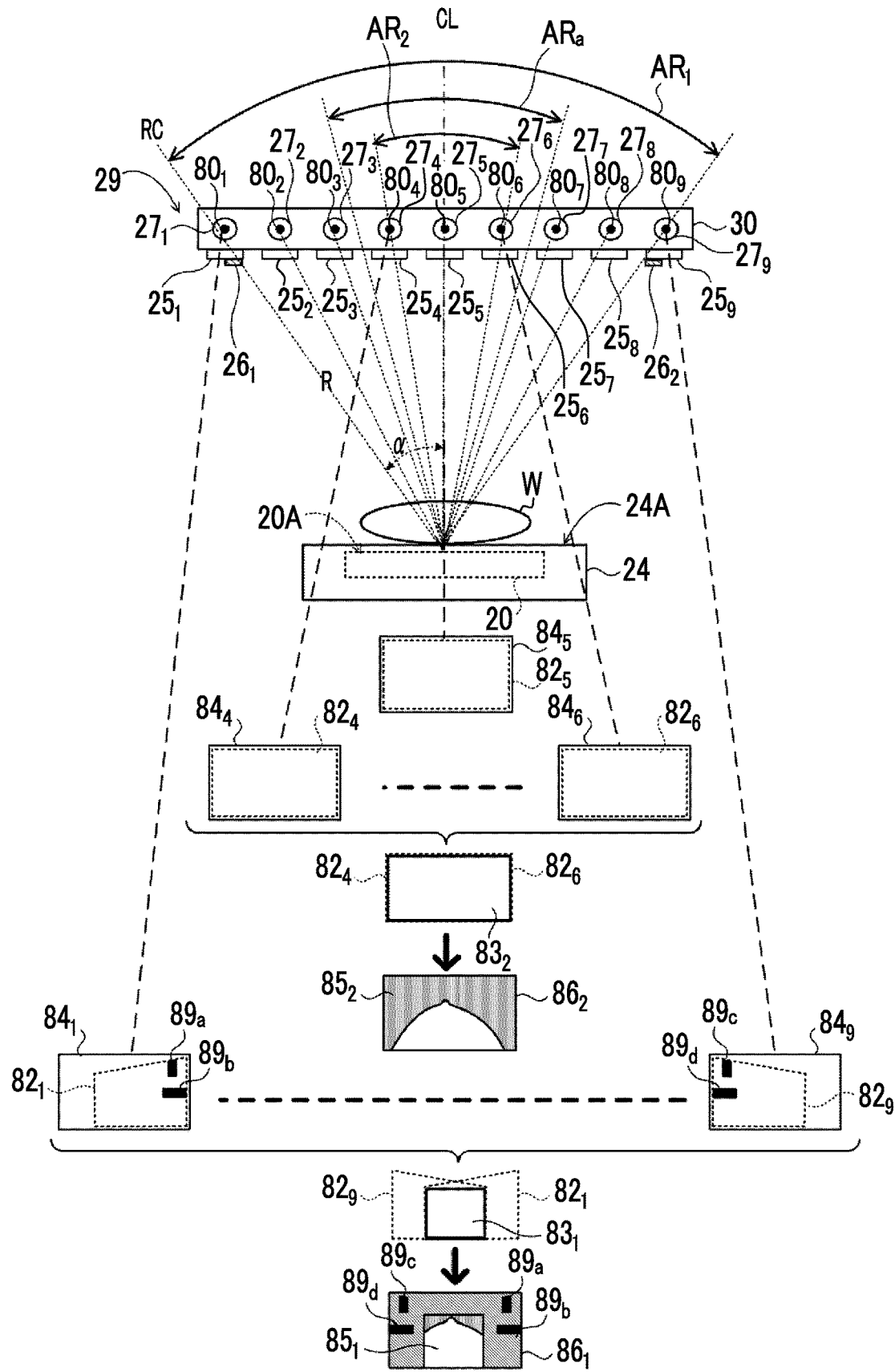
FIG. 5 is a diagram illustrating an example of tomosynthesis imaging in a mammography apparatus according to the embodiment.

Further, for the capture of radiographic images, the mammography apparatus 10 according to this embodiment can perform so-called tomosynthesis imaging. FIG. 5 is a diagram illustrating an example of the tomosynthesis imaging. In addition, the compression plate 38 is not illustrated in FIG. 5. As described above, each of the radiation tubes 27 of the radiation source 29 is disposed at a predetermined irradiation position 80. In other words, in the example illustrated in FIG. 5, the radiation tubes $27_1$ to $27_9$ are disposed at the irradiation positions $80_1$ to $80_9$ where the radiation R is incident on the detection surface 20A of the radiation detector 20 at different angles, respectively. At each of the irradiation positions $80_1$ to $80_9$, the radiation R is sequentially emitted from the radiation source 29 to a breast W in response to an instruction from the console 12, and the radiation detector 20 captures projection images. In the radiography system 1, the radiation R is sequentially emitted from the radiation tubes $27_1$ to $27_9$ to sequentially capture the projection images $84_1$ to $84_9$. In the example illustrated in FIG. 5, nine projection images 84 are obtained. Further, in this embodiment, in a case in which a radiographic image is generically referred to regardless of the type, such as a projection image and a tomographic image which will be described below, it is simply referred to as a "radiographic image".

In addition, as illustrated in FIG. 5, the irradiation angle of the radiation R means an angle α formed between a normal line CL to the detection surface 20A of the radiation detector 20 and a radiation axis RC. That is, the irradiation angle of the radiation R means the incident angle of the radiation axis RC with respect to the detection surface 20A of the radiation detector 20. The radiation axis RC means an axis that connects the focus of the radiation tube 27 of the radiation source 29 at each irradiation position 80 and a preset position such as the center of the detection surface 20A. Further, here, it is assumed that the detection surface 20A of the radiation detector 20 is substantially parallel to the imaging surface 24A. Hereinafter, a predetermined range in which the irradiation angles are different in the tomosynthesis imaging as illustrated in FIG. 5 is referred to as an "irradiation angle range".

Further, FIG. 5 illustrates object regions $82_1$, $82_4$, $82_5$, $82_6$, and $82_9$ which are included in projection images $84_1$, $84_4$, $84_5$, $84_6$, and $84_9$ obtained by the radiation tube 27 at the irradiation positions $80_1$, $80_4$, $80_5$, $80_6$, and $80_9$, respectively. The object region 82 corresponds to an irradiation field 102 limited by the collimator 25. Specifically, the object region 82 corresponds to the irradiation field 102 of the radiation R on the detection surface 20A of the radiation detector 20. In addition, in this embodiment, in a case in which each of the irradiation positions 80, the object regions 82, the projection images 84, and the tomographic images 86 is distinguished, numbers "1 to 9" indicating the components are added to the reference numerals. Further, in the following description, for simplicity, the projection image 84 obtained by the radiation R emitted by the radiation tube 27 disposed at a certain irradiation position 80 is simply referred to as "a projection image 84 obtained at the irradiation position 80".

The object region $82_5$ which is included in the projection image $84_5$ obtained at the irradiation position $80_5$, where the irradiation angle is 0 degrees, along the normal line CL has the range and size in which the entire image of the breast W, which is the object, can be captured.

As the angle α becomes larger, in other words, as the irradiation angle of the radiation R obliquely incident on the detection surface 20A of the radiation detector 20 becomes larger, the influence of the oblique incidence of the radiation R becomes larger, and the irradiation field 102 of the radiation R becomes narrower. Therefore, as illustrated in FIG. 5, as the angle α becomes larger, the object region 82 included in the projection image 84 becomes narrower. In other words, in a case in which the radiation source 29 is located at the irradiation position 80 having a relatively large irradiation angle, the influence of the oblique incidence of the radiation R becomes large. Therefore, the object region 82 included in the obtained projection image 84 is narrower than the object region $82_5$. In the example illustrated in FIG. 5, both the object region $82_1$ included in the projection image $84_1$ obtained at the irradiation position $80_1$ having the largest irradiation angle and the object region $82_9$ included in the projection image $84_9$ obtained at the irradiation position $80_9$ are narrower than the object region $82_5$. Specifically, the object region $82_1$ and the object region $82_9$ have a shape in which a region on the side where the radiation source 29 is located during imaging has missed. As described above, for example, the size of the object region 82 included in the projection image 84 varies depending on the irradiation position 80.

In a case in which a tomographic image 86 is reconstructed using a plurality of projection images 84 obtained by the tomosynthesis imaging, a reconstructed region that is used during reconstruction depends on the object region 82 in each projection image 84. Specifically, the reconstructed region is limited to a common partial region (hereinafter, referred to as a "partial region") of the object regions 82 included in all of the projection images 84 used to generate the tomographic image 86.

As illustrated in FIG. 5, in the case of the irradiation position 80 where the irradiation angle is relatively small, even though the radiation R emitted from the radiation source 29 is obliquely incident on the detection surface 20A of the radiation detector 20, the object region 82 having the same shape and size as the object region $82_5$ is obtained. In a case in which the object region 82 included in the projection image 84 obtained at each of the plurality of irradiation positions 80 is equivalent to the object region $82_5$, a partial region 83, that is, a reconstructed region 85 is also equivalent to the object region $82_5$. In this case, since the entire object region 82 included in each projection image 84 is regarded as the partial region 83, it cannot be said to be a "part" in a strict sense, but is referred to as a "part" for convenience of explanation. In a case in which the reconstructed region 85 is equivalent to the object region $82_5$, the tomographic image 86 is an image in which the entire object is included. Further, the "entire object" included in the tomographic image 86 means, for example, a portion captured by the radiation detector 20 in a case in which radiation is emitted at the irradiation position where the irradiation angle α is 0 degrees in the object to be imaged such as the breast. Furthermore, the entire object is about a plane in which the radiation R is projected onto the object. The entire object does not mean, for example, the entire breast, but means at least the entire region of the object desired by the user for image interpretation. For example, the entire object also includes a region in which an end portion of the object that is not required for interpretation or the like has missed.

As described above, the irradiation angle range, which is the range of the irradiation positions 80 where the projection images 84 that can make the reconstructed region 85 in the tomographic image 86 equivalent to the object region $82_5$ are obtained, is referred to as an overall imaging irradiation angle range $AR_a$ (See FIG. 5). That is, the overall imaging irradiation angle range $AR_a$ means an irradiation angle range in which the tomographic image 86 including the entire object can be obtained in a case in which the tomographic image 86 is generated using the projection images 84 obtained at each of the plurality of irradiation positions 80. Strictly speaking, the overall imaging irradiation angle range $AR_a$ means the maximum irradiation angle range in which the tomographic image 86 including the entire object can be obtained.

In a case in which the irradiation angle range is wider than the overall imaging irradiation angle range $AR_a$, the reconstructed region 85 in the tomographic image 86 is narrower than the object region $82_5$. Therefore, the tomographic image 86 is an image in which a part of the object is included.

In FIG. 5, a first irradiation angle range $AR_1$ is illustrated as an irradiation angle range wider than the overall imaging irradiation angle range $AR_a$. In a case in which the irradiation angle range is the first irradiation angle range $AR_1$, a partial region $83_1$ common to the object regions $82_1$ to $82_9$ included in the projection images $84_1$ to $84_9$ obtained at each of the irradiation positions $80_1$ to $80_9$ corresponds to a reconstructed region $85_1$ in a case in which a first tomographic image $86_1$ is generated. The partial region $83_1$, that is, the reconstructed region $85_1$ is smaller than the object regions $82_1$ to $82_9$ included in the projection images $84_1$ to $84_9$.

In the first tomographic image $86_1$, the reconstructed region $85_1$ is a region in which the object can be included. Therefore, the first tomographic image $86_1$ is an image in which a part of the object is included. For example, FIG. 5 illustrates the first tomographic image $86_1$ in which a part of the breast W, which is the object, is included.

The resolution of the tomographic image 86 depends on the irradiation angle range. As the irradiation angle range becomes wider, the resolution of the tomographic image 86 becomes higher. Therefore, the first tomographic image $86_1$ generated by the plurality of projection images $84_1$ to $84_9$ obtained by the tomosynthesis imaging in the first irradiation angle range $AR_1$ is a high-resolution image. The first tomographic image $86_1$ according to this embodiment is an example of a partial tomographic image according to the present disclosure.

On the other hand, in a case in which the irradiation angle range is equal to or narrower than the overall imaging irradiation angle range $AR_a$, the reconstructed region 85 in the tomographic image 86 is equivalent to the object region $82_5$. Therefore, the tomographic image 86 is an image in which the entire object is included.

In FIG. 5, a second irradiation angle range $AR_2$ is illustrated as an irradiation angle range that is equal to or narrower than the overall imaging irradiation angle range $AR_a$. In a case in which the irradiation angle range is the second irradiation angle range $AR_2$, a partial region $83_2$ common to the object regions $82_4$ to $82_6$ included in the projection images $84_4$ to $84_6$ obtained at each of the irradiation positions $80_4$ to $80_6$ corresponds to a reconstructed region $85_2$ in a case in which a second tomographic image $86_2$ is generated. The partial region $83_2$, that is, the reconstructed region $85_2$ is equivalent to the object regions $82_4$ to $82_6$ included in the projection images $84_4$ to $84_6$.

In the second tomographic image $86_2$, the reconstructed region $85_2$ is a region in which the object can be included. Therefore, the second tomographic image $86_2$ is an image in which the entire object is included. For example, FIG. 5 illustrates the second tomographic image $86_2$ in which the entire breast W, which is the object, is included.

The resolution of the tomographic image 86 depends on the irradiation angle range. As the irradiation angle range becomes narrower, the resolution of the tomographic image 86 becomes lower. Therefore, the second tomographic image $86_2$ generated using the plurality of projection images $84_4$ to $84_6$ obtained by the tomosynthesis imaging in the second irradiation angle range $AR_2$ has a lower resolution than the first tomographic image $86_1$. The second tomographic image $86_2$ according to this embodiment is an example of an entire tomographic image according to the present disclosure.

As described above, in a case in which the irradiation angle range is equal to or narrower than the overall imaging irradiation angle range $AR_a$, the tomographic image 86 generated by the projection images 84 obtained at each irradiation position 80 is a tomographic image in which the entire object is included. In a case in which the irradiation angle range is wider than the overall imaging irradiation angle range $AR_a$, the tomographic image 86 generated by the projection images 84 obtained at each irradiation position 80 is a tomographic image which includes a part of the object, but has a high resolution.

Figure 6A:
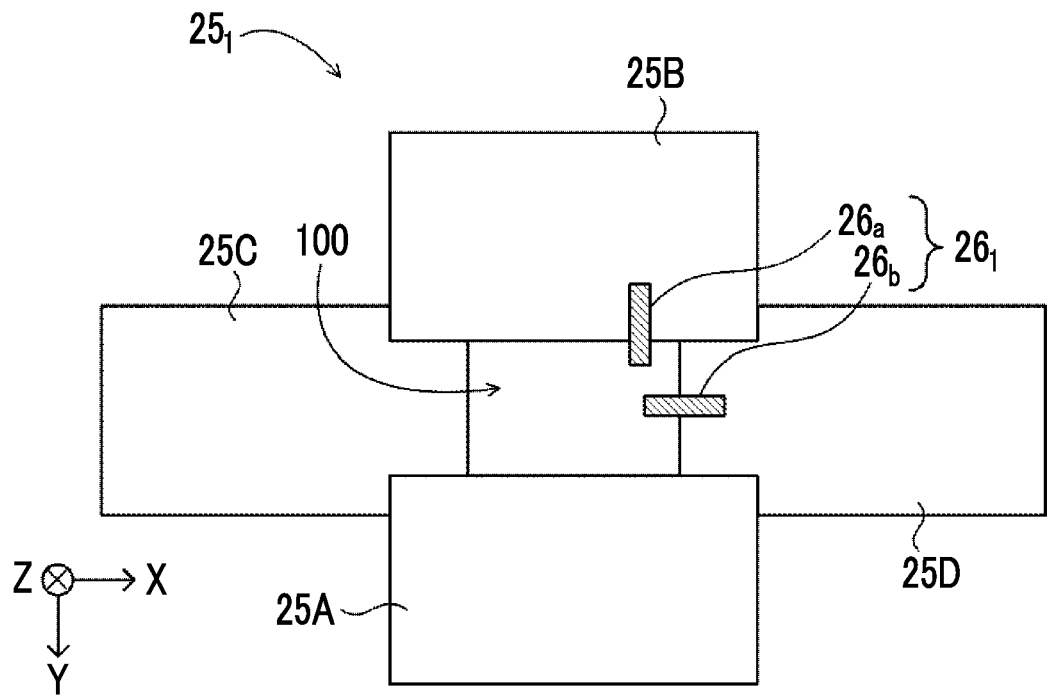
FIG. 6A is a plan view illustrating an example of a correction marker provided in the collimator as viewed from an imaging table.

Further, as illustrated in FIG. 5, the collimator $25_1$ that is provided so as to correspond to the radiation tube $27_1$ is provided with the correction marker $26_1$. FIG. 6A is a plan view illustrating an example of the correction marker $26_1$ provided in the collimator $25_1$ as viewed from the imaging table 24. As illustrated in FIG. 6A, the correction marker $26_1$ includes a first correction marker $26_a$ and a second correction marker $26_b$. The correction marker $26_1$ is provided in an irradiation path of the radiation R that has passed through the opening portion 100 of the collimator $25_1$. Specifically, the first correction marker $26_a$ is provided on the blade 25B in a state in which a part thereof protrudes to the inside of the opening portion 100. In addition, the second correction marker $26_b$ is provided on the blade 25D in a state in which a part thereof protrudes to the inside of the opening portion 100. Therefore, as illustrated in FIG. 5, a marker image $89_a$ of the first correction marker $26_a$ and a marker image $89_b$ of the second correction marker $26_b$ are included in the projection image $84_1$ obtained at the irradiation position $80_1$. Further, the marker images $89_a$ and $89_b$ are included in a region other than the reconstructed region $85_1$ in the first tomographic image $86_1$.

Figure 6B:
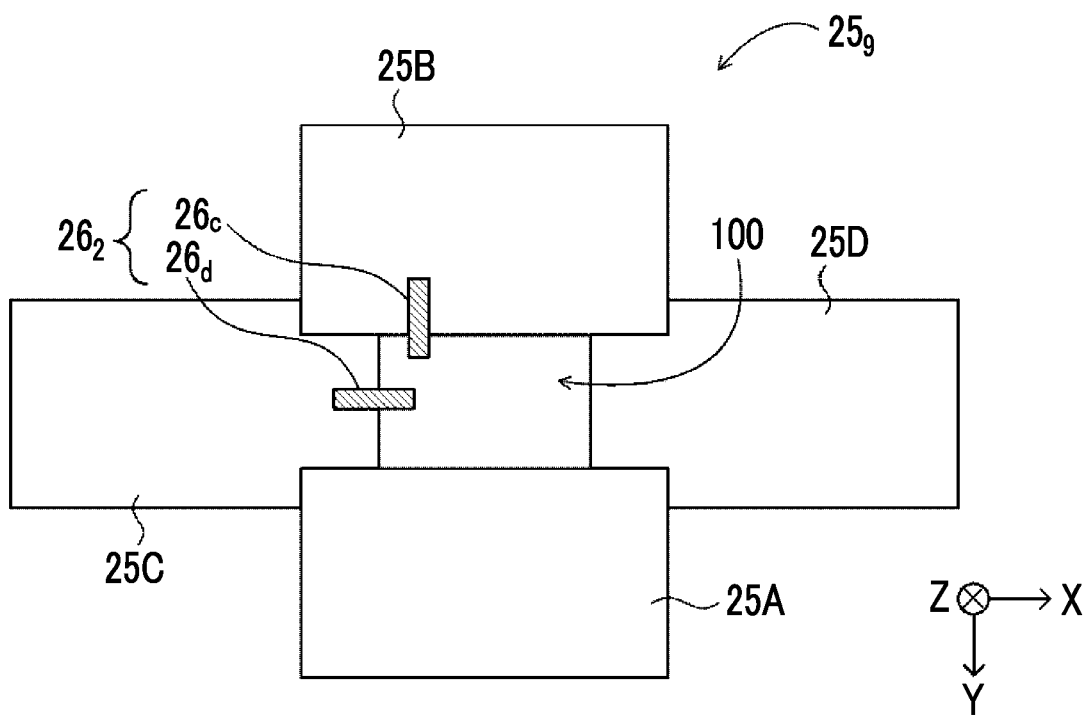
FIG. 6B is a plan view illustrating an example of the correction marker provided in the collimator as viewed from the imaging table.

Further, as illustrated in FIG. 5, the collimator $25_9$ that is provided so as to correspond to the radiation tube $27_9$ is provided with the correction marker $26_2$. FIG. 6B is a plan view illustrating an example of the correction marker $26_2$ provided on the collimator $25_9$ as viewed from the imaging table 24. As illustrated in FIG. 6B, the correction marker $26_2$ includes a first correction marker $26_c$ and a second correction marker $26_d$. The correction marker $26_2$ is provided in the irradiation path of the radiation R that has passed through the opening portion 100 of the collimator $25_9$. Specifically, the first correction marker $26_c$ is provided on the blade 25B in a state in which a part thereof protrudes to the inside of the opening portion 100. In addition, the second correction marker $26_d$ is provided on the blade $25_c$ in a state in which a part thereof protrudes to the inside of the opening portion 100. Therefore, as illustrated in FIG. 5, a marker image $89_c$ of the first correction marker $26_c$ and a marker image $89_d$ of the second correction marker $26_d$ are included in the projection image $84_9$ obtained at the irradiation position $80_9$. Further, the marker images $89_c$ and $89_d$ are included in the region other than the reconstructed region $85_1$ in the first tomographic image $86_1$.

The first correction markers $26_a$ and $26_c$ are markers that are used to detect the positional deviation of the focus of the radiation tube 27 in the left-right direction. In addition, the second correction markers $26_b$ and $26_d$ are markers that are used to detect the positional deviation of the focus of the radiation tube 27 in a direction intersecting the left-right direction. Further, the "left-right direction" means a direction corresponding to the left and right sides of the subject with respect to the mammography apparatus 10 and means the X-axis direction in this embodiment. Furthermore, the "direction intersecting the left-right direction" means a direction connecting the chest wall side and the anti-chest wall side of the subject in the mammography apparatus 10 and means the Y-axis direction in this embodiment. In the following description, the direction intersecting the left-right direction is referred to as an "intersecting direction".

Figure 7:
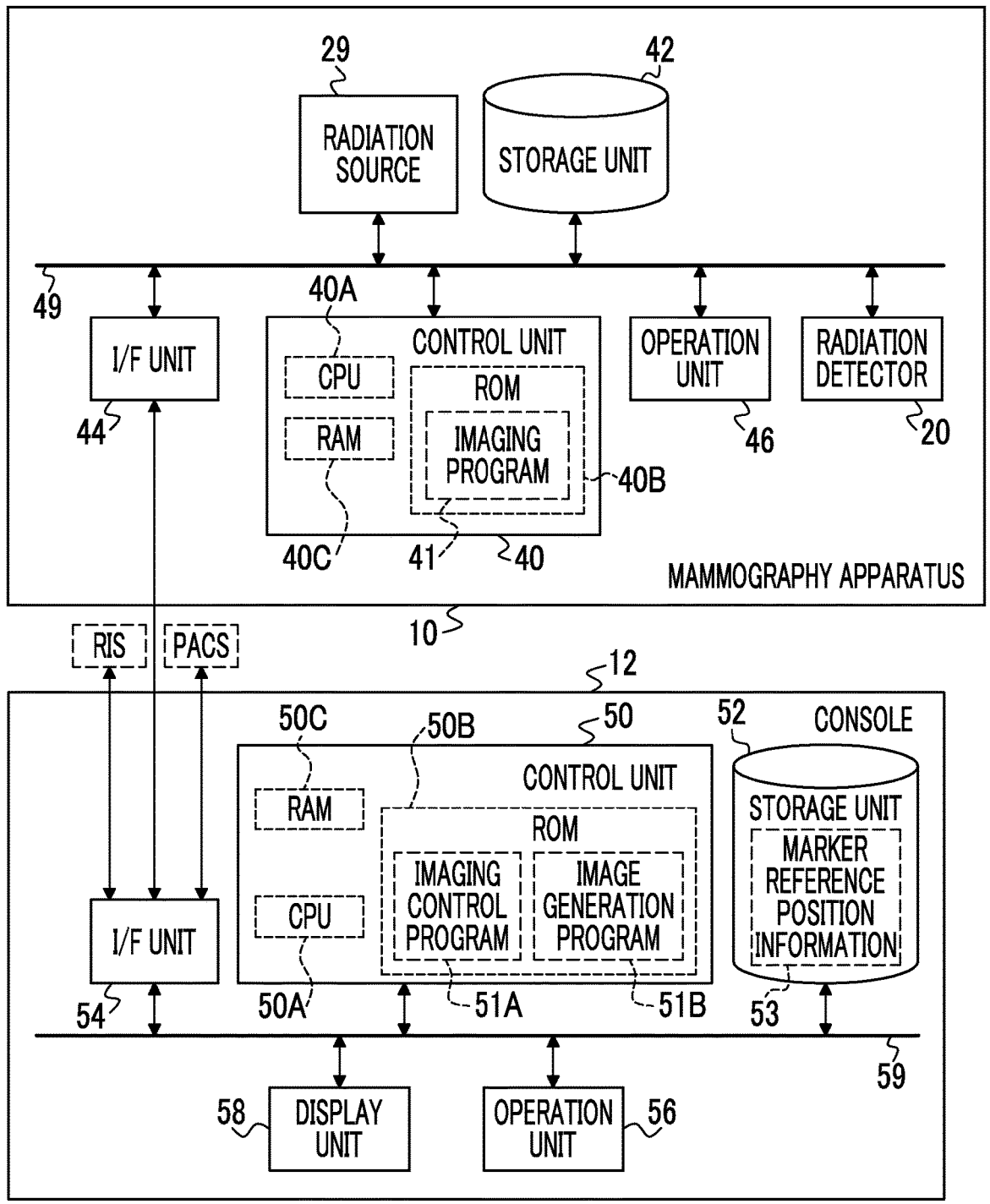
FIG. 7 is a block diagram illustrating an example of the configuration of the mammography apparatus and a console according to the embodiment.

Further, FIG. 7 is a block diagram illustrating an example of the configuration of the mammography apparatus 10 and the console 12 according to the embodiment. As illustrated in FIG. 7, the mammography apparatus 10 according to this embodiment further comprises a control unit 40, a storage unit 42, an interface (I/F) unit 44, and an operation unit 46. The control unit 40, the storage unit 42, the I/F unit 44, and the operation unit 46 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. For example, various programs including an imaging program 41 which is executed by the CPU 40A and performs control related to the capture of a radiographic image are stored in the ROM 40B in advance. The RAM 40C temporarily stores various kinds of data.

For example, the image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 7, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs including an imaging control program 51A and an image generation program 51B executed by the CPU 50A are stored in the ROM 50B in advance. The RAM 50C temporarily stores various kinds of data. In this embodiment, the CPU 50A is an example of a processor according to the present disclosure, and the console 12 is an example of an image processing device according to the present disclosure. In addition, the image generation program 51B according to this embodiment is an example of an image processing program according to the present disclosure.

For example, the image data of the radiographic image captured by the mammography apparatus 10 and various other kinds of information are stored in the storage unit 52. Further, marker reference position information 53 has been stored in the storage unit 52 according to this embodiment. The marker reference position information 53 is information indicating the reference positions of the marker images $89_a$ to $89_d$ included in the projection images 84. Specifically, the marker reference position information 53 includes the positions of the marker images $89_a$ and $89_b$ of the first correction marker $26_a$ and the second correction marker $26_b$ included in the projection image $84_1$ in a case in which the focus of the radiation tube $27_1$ is located at a predetermined position such as a design position. Furthermore, the marker reference position information 53 includes the positions of the marker images $89_c$ and $89_d$ of the first correction marker $26_c$ and the second correction marker $26_d$ included in the projection image $84_9$ in a case in which the focus of the radiation tube $27_9$ is located at a predetermined position such as a design position. A specific example of the storage unit 52 is an HDD, an SSD, or the like.

The operation unit 56 is used by the user to input instructions, which are related to, for example, the capture of a radiographic image and include an instruction to emit the radiation R, various kinds of information, and the like. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 8:
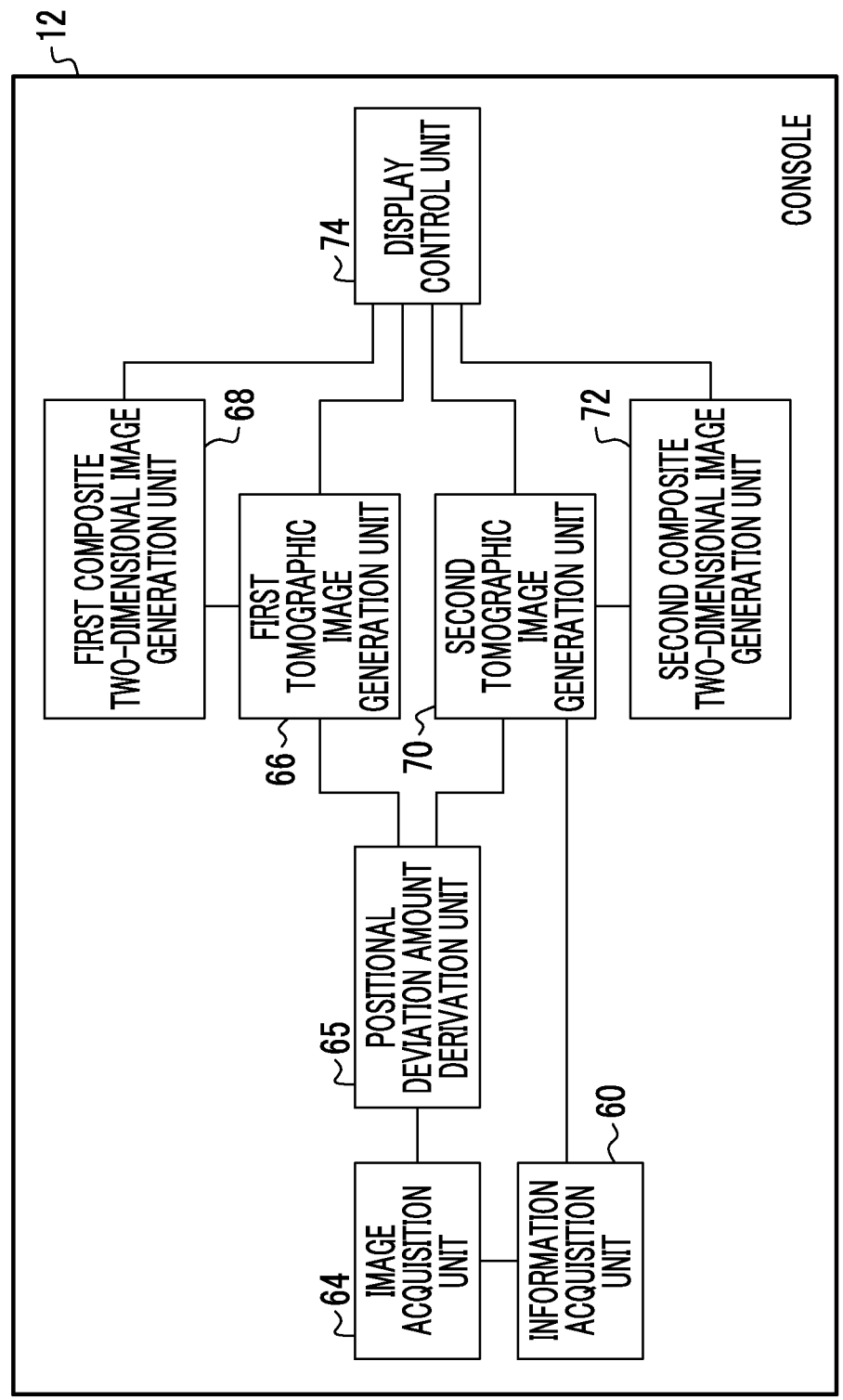
FIG. 8 is a functional block diagram illustrating an example of the functions of the console according to the embodiment.

The console 12 according to this embodiment has a function of generating a tomographic image from the projection images obtained by the tomosynthesis imaging. FIG. 8 is a functional block diagram illustrating an example of the configuration of the console 12 according to this embodiment related to the function of controlling the irradiation angle range and the function of generating a tomographic image. As illustrated in FIG. 8, the console 12 comprises an information acquisition unit 60, an image acquisition unit 64, a positional deviation amount derivation unit 65, a first tomographic image generation unit 66, a first composite two-dimensional image generation unit 68, a second tomographic image generation unit 70, a second composite two-dimensional image generation unit 72, and a display control unit 74. Further, in the console 12 according to this embodiment, the CPU 50A of the control unit 50 executes the image generation program 51B stored in the ROM 50B to function as the information acquisition unit 60, the image acquisition unit 64, the positional deviation amount derivation unit 65, the first tomographic image generation unit 66, the first composite two-dimensional image generation unit 68, the second tomographic image generation unit 70, the second composite two-dimensional image generation unit 72, and the display control unit 74.

The information acquisition unit 60 has a function of acquiring overall imaging information indicating the overall imaging irradiation angle range $AR_a$. As described above, the overall imaging irradiation angle range $AR_a$ is the irradiation angle range in which the projection images 84 capable of generating the tomographic image 86 including the entire object can be obtained. The overall imaging irradiation angle range $AR_a$ depends on the thickness of the object and the area of the object. The "thickness of the object" means the thickness of the breast compressed by the compression plate 38. In this embodiment, the "thickness of the object" means the distance from the imaging surface 24A of the imaging table 24 to a compression surface of the compression plate 38 which compresses the breast. In addition, the "area of the object" means the area of the breast that is compressed by the compression plate 38 and is irradiated with the radiation R. In this embodiment, the "area of the object" means the contact area of the breast with the imaging surface 24A of the imaging table 24 or the contact area of the breast with the compression plate 38.

However, in a case in which the breast is large, the area of the breast compressed by the compression plate 38 is relatively large, and the thickness of the breast is relatively large. On the other hand, in a case in which the breast is small, the area of the breast compressed by the compression plate 38 is relatively small, and the thickness of the breast is relatively small. Therefore, for example, in this embodiment, the overall imaging irradiation angle range $AR_a$ is determined according to the size of the breast. Specifically, the irradiation angle range correspondence relationship information in which the sizes of the breast, such as a "large" size, a "medium" size, and a "small" size, are associated with the overall imaging irradiation angle range $AR_a$ is obtained in advance. The information acquisition unit 60 acquires the overall imaging information indicating the overall imaging irradiation angle range $AR_a$ with reference to the irradiation angle range correspondence relationship information.

First, the information acquisition unit 60 acquires information indicating the size of the breast, such as a "large" size, a "medium" size, and a "small" size, input by the user through the operation unit 56. The information acquisition unit 60 acquires the overall imaging information indicating the overall imaging irradiation angle range $AR_a$ which corresponds to the size of the breast with reference to the irradiation angle range correspondence relationship information. Then, the information acquisition unit 60 outputs the acquired overall imaging information to the image acquisition unit 64 and the second tomographic image generation unit 70.

The image acquisition unit 64 has a function of acquiring a projection image group including a plurality of projection images 84 obtained by the tomosynthesis imaging in an irradiation angle range wider than the overall imaging irradiation angle range $AR_a$. Specifically, the image acquisition unit 64 according to this embodiment acquires the projection images $84_1$ to $84_9$ obtained by the tomosynthesis imaging in the first irradiation angle range $AR_1$ as the irradiation angle range wider than the overall imaging irradiation angle range $AR_a$ corresponding to the overall imaging information input from the information acquisition unit 60. The image acquisition unit 64 outputs image data indicating the acquired projection images $84_1$ to $84_9$ to the positional deviation amount derivation unit 65.

The positional deviation amount derivation unit 65 derives the positional deviation amount of the focus of the radiation tube 27 used for the tomosynthesis imaging on the basis of the position of the marker image 89 in the projection image 84 and the reference position of the marker image 89.

Figure 9A:
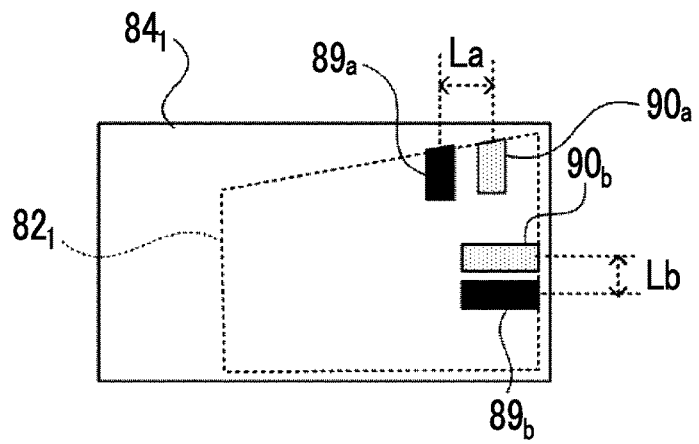
FIG. 9A is a diagram illustrating the derivation of a positional deviation amount by a positional deviation amount derivation unit.
Figure 9B:
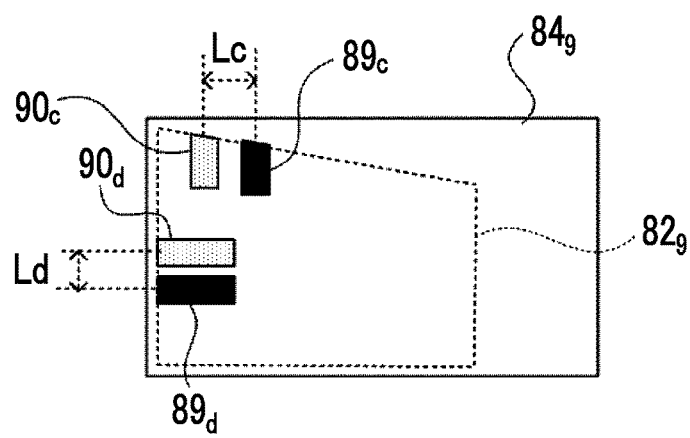
FIG. 9B is a diagram illustrating the derivation of the positional deviation amount by the positional deviation amount derivation unit.

The positional deviation amount derivation unit 65 according to this embodiment derives the amount of derivation between the reference position of the marker image $89_a$ acquired from the marker reference position information 53 and the position of the marker image $89_a$ included in the projection image $84_1$. FIG. 9A illustrates the marker image $89_a$ included in the projection image $84_1$ and a reference image $90_a$ indicating the reference position of the marker image $89_a$. In addition, for convenience of explanation, the reference positions of the marker images $89_a$, $89_b$, $89_c$, and $89_d$ are illustrated as the reference images $90_a$, $90_b$, $90_c$, and $90_d$ on the projection image $84_1$ or $84_9$, respectively. However, the reference images $90_a$, $90_b$, $90_c$, and $90_d$ are not included in the projection image $84_1$ or $84_9$. The positional deviation amount derivation unit 65 derives a positional deviation amount La between the marker image $89_a$ and the reference image $90_a$. In addition, the positional deviation amount derivation unit 65 derives the amount of derivation between the reference position of the marker image $89_c$ acquired from the marker reference position information 53 and the position of the marker image $89_c$ included in the projection image $84_9$. FIG. 9B illustrates the marker image $89_c$ and the reference image $90_c$ indicating the reference position of the marker image $89_c$ in the projection image $84_9$. The positional deviation amount derivation unit 65 derives a positional deviation amount Lc between the marker image $89_c$ and the reference image $90_c$. Further, the positional deviation amount derivation unit 65 derives the positional deviation amount of the focus of the radiation tube 27 in the left-right direction on the basis of the derived positional deviation amounts La and Lc.

In some cases, the position of the focus of the radiation tube 27 changes from a predetermined position such as a design position. For example, in a case in which the arm portion 33 supporting the radiation source accommodation portion 30 of the radiation emitting unit 28 is deformed due to distortion or the like, the position of the focus of the radiation tube 27 changes from the predetermined position. In a case in which the arm portion 33 is distorted in this way, positional deviation generally occurs in the focuses of the plurality of radiation tubes 27 in the radiation emitting unit 28 with the distortion of the arm portion 33. That is, in a case in which the positional deviation amount of at least one or more radiation tubes 27 among the plurality of radiation tubes 27 can be derived, it is possible to estimate the positional deviation amounts of the other radiation tubes 27.

Therefore, in this embodiment, the amounts of positional deviation of the focuses of all of the radiation tubes 27 in the radiation emitting unit 28 are associated with the amounts of positional deviation of the focuses of the radiation tubes 27 at the irradiation positions 80 at both ends of the irradiation angle range. Specifically, in this embodiment, left-right-direction positional deviation amount correspondence relationship information indicating the correspondence relationship among the positional deviation amount La of the focus of the radiation tube $27_1$, the positional deviation amount Lc of the focus of the radiation tube $27_9$, and the positional deviation amount of the focus of each of the radiation tubes $27_1$ to $27_9$ in the left-right direction is obtained in advance. The left-right-direction positional deviation amount correspondence relationship information is stored in, for example, the storage unit 52 or the like. The positional deviation amount derivation unit 65 derives the positional deviation amount of the focus of each of the radiation tubes $27_1$ to $27_9$ in the left-right direction which is associated with the derived positional deviation amounts La and Lc with reference to the left-right-direction positional deviation amount correspondence relationship information.

In addition, the positional deviation amount derivation unit 65 according to this embodiment derives the amount of derivation between the reference position of the marker image $89_b$ acquired from the marker reference position information 53 and the position of the marker image $89_b$ included in the projection image $84_1$. FIG. 9A illustrates the marker image $89_b$ included in the projection image $84_1$ and the reference image $90_b$ indicating the reference position of the marker image $89_b$. The positional deviation amount derivation unit 65 derives the positional deviation amount Lb between the marker image $89_b$ and the reference image $90_b$. Further, the positional deviation amount derivation unit 65 derives the amount of derivation between the reference position of the marker image $89_d$ acquired from the marker reference position information 53 and the position of the marker image $89_d$ included in the projection image $84_9$. FIG. 9B illustrates the marker image $89_d$ and the reference image $90_d$ indicating the reference position of the marker image $89_d$ in the projection image $84_9$. The positional deviation amount derivation unit 65 derives the positional deviation amount Ld between the marker image $89_d$ and the reference image $90_d$. In addition, the positional deviation amount derivation unit 65 derives the positional deviation amount of the focus of the radiation tube 27 in the intersecting direction on the basis of the derived positional deviation amounts Lb and Ld.

Similar to the derivation of the positional deviation amount in the left-right direction, in this embodiment, the positional deviation amounts of the focuses of all of the radiation tubes 27 in the radiation emitting unit 28 are associated with the positional deviation amounts of the focuses of the radiation tubes 27 at the irradiation positions 80 at both ends of the irradiation angle range. Specifically, in this embodiment, intersecting-direction positional deviation amount correspondence relationship information indicating the correspondence relationship among the positional deviation amount Lb of the focus of the radiation tube $27_1$, the positional deviation amount Ld of the focus of the radiation tube $27_9$, and the positional deviation amount of the focus of each of the radiation tubes $27_1$ to $27_9$ in the intersecting direction is obtained in advance. The intersecting-direction positional deviation amount correspondence relationship information is stored in, for example, the storage unit 52 or the like. The positional deviation amount derivation unit 65 derives the positional deviation amount of the focus of each of the radiation tubes $27_1$ to $27_9$ in the intersecting direction which is associated with the derived positional deviation amounts Lb and Ld with reference to the intersecting-direction positional deviation amount correspondence relationship information.

The positional deviation amount derivation unit 65 outputs the derived positional deviation amount of the focus of each of the radiation tubes 27 and the positional deviation amount thereof in the intersecting direction to the first tomographic image generation unit 66 and the second tomographic image generation unit 70.

The first tomographic image generation unit 66 has a function of generating a plurality of first tomographic images $86_1$ including a part of the object, using a plurality of projection images $84_1$ to $84_9$ obtained by the tomosynthesis imaging in the first irradiation angle range $AR_1$ among the projection images included in the acquired projection image group on the basis of the position of the marker image 89 included in the projection image 84 and the reference position of the marker image 89.

Specifically, the first tomographic image generation unit 66 corrects the positions of the focuses of the radiation tubes $27_1$ to $27_9$ on the basis of the positional deviation amounts in the left-right direction and the intersecting direction derived by the positional deviation amount derivation unit 65. Then, the first tomographic image generation unit 66 reconstructs the first tomographic image $86_1$ from the projection images $84_1$ to $84_9$ using the corrected position of the focus of each of the radiation tubes $27_1$ to $27_9$. In addition, a method by which the first tomographic image generation unit 66 generates the plurality of first tomographic images $86_1$ is not particularly limited, and a known method may be used. For example, reconstruction may be performed by a back projection method, such as a filter back projection (FBP) method or an iterative reconstruction method, or a known technique may be applied. The slice thickness (hereinafter, referred to as a "first slice thickness") of the tomographic images $86_1$ generated by the first tomographic image generation unit 66 is not particularly limited. In addition, as the resolution of the tomographic image becomes higher, the slice thickness can become smaller. Therefore, in this embodiment, the first slice thickness is smaller than the slice thickness of the second tomographic image $86_2$ (hereinafter, referred to as a "second slice thickness"). Specifically, the first slice thickness can be determined according to, for example, the size of a region of interest, the quality of the radiographic image, the processing load of arithmetic processing in the generation, and an instruction from the user. The first tomographic image generation unit 66 outputs image data indicating the generated plurality of first tomographic images $86_1$ to the first composite two-dimensional image generation unit 68 and the display control unit 74.

The first composite two-dimensional image generation unit 68 has a function of generating a first composite two-dimensional image obtained by combining at least some of the plurality of first tomographic images $86_1$. The first composite two-dimensional image generation unit 68 outputs image data indicating the generated first composite two-dimensional image to the display control unit 74.

Further, a method by which the first composite two-dimensional image generation unit 68 generates the first composite two-dimensional image is not particularly limited, and a known method may be used. For example, the first composite two-dimensional image generation unit 68 uses the method described in the specification of U.S. Pat. No. 8,983,156B. U.S. Pat. No. 8,983,156B discloses a technique that blends (combines) a region of interest (ROI) detected from a tomographic image with a two-dimensional image to a composite two-dimensional image in which a lesion or the like detected from the tomographic image has been reflected. In addition, a method for detecting the region of interest from the tomographic image is not particularly limited. For example, a method that extracts the region of interest from the tomographic image using a known computer-aided diagnosis (hereinafter, referred to as CAD) algorithm is given as an example. In the CAD algorithm, preferably, the probability (for example, likelihood) that a pixel in the tomographic image will be the region of interest is derived, and the pixel is detected as a pixel constituting the image of the region of interest in a case in which the probability is equal to or greater than a predetermined threshold value. Further, for example, a method may be used which extracts the region of interest from the tomographic image by a filtering process or the like using a filter for extracting the region of interest.

Further, as a method by which the first composite two-dimensional image generation unit 68 generates the first composite two-dimensional image, for example, a method may be used which generates a composite two-dimensional image by projecting a plurality of tomographic images, or at least one of the plurality of tomographic images and at least one of a plurality of projection images in a depth direction in which the tomographic planes of the breast are arranged or by using a minimum intensity projection method, which is disclosed in JP2014-128716A. In addition, for example, a method may be used which generates a composite two-dimensional image by reconstructing a plurality of tomographic images, or at least one of the plurality of tomographic images and at least one of a plurality of projection images using any one of a filtered back projection method, a maximum likelihood reconstruction method, an iterative reconstruction method, a reconstruction method using an algebraic method, or a three-dimensional reconstruction method, which is disclosed in JP6208731B.

On the other hand, the second tomographic image generation unit 70 has a function of generating a plurality of second tomographic images $86_2$ including the entire object, using a plurality of projection images $84_4$ to $84_6$ obtained by the tomosynthesis imaging in the second irradiation angle range $AR_2$ among the projection images included in the acquired projection image group on the basis of the position of the marker image 89 included in the projection image 84 and the reference position of the marker image 89. Specifically, the second tomographic image generation unit 70 corrects the position of the focus of each of the radiation tubes $27_4$ to $27_6$ on the basis of the positional deviation amounts in the left-right direction and the intersecting direction derived by the positional deviation amount derivation unit 65. Specifically, the second tomographic image generation unit 70 acquires the projection images $84_4$ to $84_6$ obtained by the tomosynthesis imaging in the second irradiation angle range $AR_2$ which is an irradiation angle range equal to or narrower than the overall imaging irradiation angle range $AR_a$ corresponding to the overall imaging information input from the information acquisition unit 60. Then, the second tomographic image generation unit 70 reconstructs the second tomographic image $86_2$ from the projection images $84_4$ to $84_6$ using the corrected position of the focus of each of the radiation tubes $27_4$ to $27_6$.

The second slice thickness of the second tomographic image $86_2$ is not particularly limited. However, in this embodiment, as described above, the second slice thickness is larger than the first slice thickness. Specifically, the second slice thickness can be determined according to, for example, the size of the region of interest, the quality of the radiographic image, the processing load of arithmetic processing in the generation, and an instruction from the user. In addition, a method by which the second tomographic image generation unit 70 generates the plurality of second tomographic images $86_2$ is not particularly limited. For example, the same method as that by which the first tomographic image generation unit 66 generates the first tomographic image $86_1$ may be applied. The second tomographic image generation unit 70 outputs image data indicating the generated plurality of second tomographic images $86_2$ to the second composite two-dimensional image generation unit 72 and the display control unit 74.

The second composite two-dimensional image generation unit 72 has a function of generating a second composite two-dimensional image obtained by combining at least some of the plurality of second tomographic images $86_2$. The second composite two-dimensional image generation unit 72 outputs image data indicating the generated second composite two-dimensional image to the display control unit 74. A method by the second composite two-dimensional image generation unit 72 generates the second composite two-dimensional image is not particularly limited. For example, the same method as that by which the first composite two-dimensional image generation unit 68 generates the first composite two-dimensional image may be applied.

The display control unit 74 has a function of displaying at least one of the first tomographic image $86_1$, the second tomographic image $86_2$, the first composite two-dimensional image, or the second composite two-dimensional image on the display unit 58. The display form of these images by the display control unit 74 will be described in detail below.

Next, the operation of the console 12 in the tomosynthesis imaging will be described with reference to the drawings. After directing the mammography apparatus 10 to perform the tomosynthesis imaging (FIG. 10, Step S10), the console 12 generates various radiographic images using the projection image group obtained by the tomosynthesis imaging and displays the radiographic images on, for example, the display unit 58 (See FIG. 10, Step S12).

Figure 10:
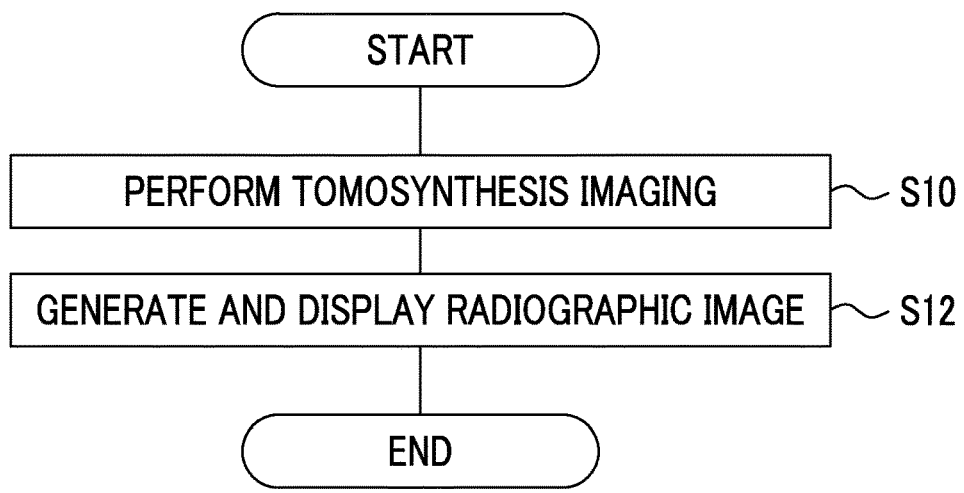
FIG. 10 is a flowchart illustrating an example of the flow of the tomosynthesis imaging.

In a case in which the tomosynthesis imaging illustrated in Step S10 of FIG. 10 is performed, first, the user positions the breast as the object on the imaging table 24 of the mammography apparatus 10 and compresses the breast with the compression plate 38. In a case in which the compression of the breast is completed, the user inputs an instruction to emit the radiation R using an irradiation button included in, for example, the operation unit 56 of the console 12. In the mammography apparatus 10, in a case in which the instruction to emit the radiation R is received, the radiation R is sequentially emitted from the radiation tubes $27_1$ to $27_9$ to the breast, and the radiation detector 20 sequentially acquires the projection images $84_1$ to $84_9$. Image data indicating each of the projection images $84_1$ to $84_9$ acquired by the radiation detector 20 is output to the console 12.

In a case in which the tomosynthesis imaging by the mammography apparatus 10 ends, the generation and display of various radiographic images by the console 12 in Step S12 of FIG. 10 are performed. The operation of the console 12 in the generation and display of various radiographic images will be described.

For example, as described above, in a case in which the tomosynthesis imaging ends, the mammography apparatus 10 according to this embodiment outputs the image data of the captured projection image group to the console 12. The console 12 stores the image data of the projection image group input from the mammography apparatus 10 in the storage unit 52.

Figure 11:
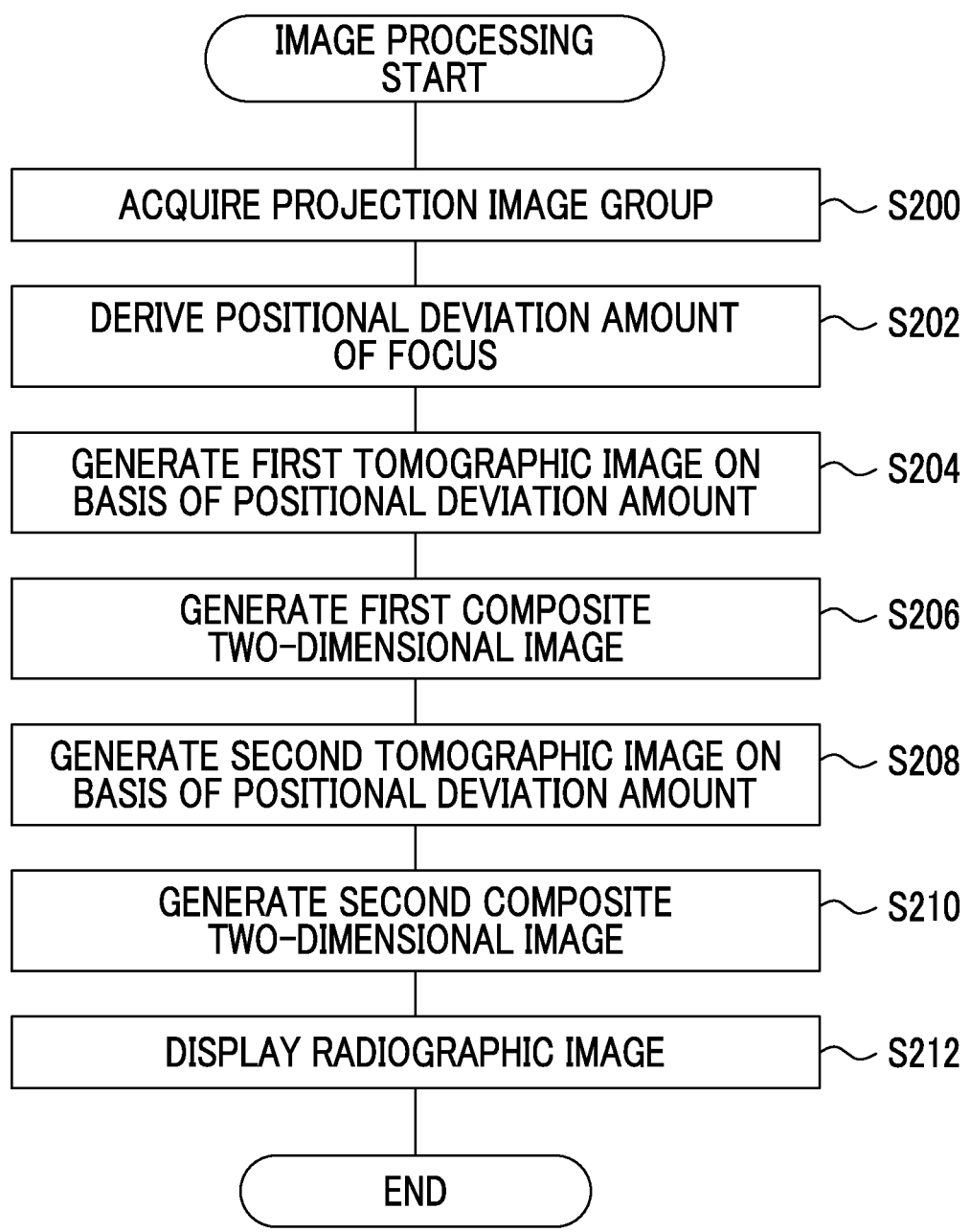
FIG. 11 is a flowchart illustrating an example of the flow of image processing by the console according to the embodiment.

After storing the image data of the projection image group in the storage unit 52, the console 12 performs image processing illustrated in FIG. 11. FIG. 11 is a flowchart illustrating an example of the flow of the image processing performed by the console 12 according to this embodiment. In the console 12 according to this embodiment, for example, the CPU 50A of the control unit 50 executes the image generation program 51B stored in the ROM 50B to perform the image processing whose example is illustrated in FIG. 11.

In Step S200 of FIG. 11, the image acquisition unit 64 acquires the projection image group. As described above, the image acquisition unit 64 according to this embodiment acquires the projection images $84_1$ to $84_9$ obtained by the tomosynthesis imaging in the first irradiation angle range $AR_1$ as the projection image group.

Then, in Step S202, the positional deviation amount derivation unit 65 derives the positional deviation amount of the focus of each radiation tube 27. As described above, the positional deviation amount derivation unit 65 according to this embodiment derives the positional deviation amount of the focus of each radiation tube 27 in the left-right direction on the basis of the marker image $89_a$ of the first correction marker $26_a$ included in the projection image $84_1$, the reference position of the first correction marker $26_a$, the marker image $89_c$ of the first correction marker $26_c$ included in the projection image $84_2$, and the reference position of the first correction marker $26_c$. In addition, the positional deviation amount derivation unit 65 derives the positional deviation amount of the focus of each radiation tube 27 in the intersecting direction on the basis of the marker image $89_b$ of the second correction marker $26_b$ included in the projection image $84_1$, the reference position of the second correction marker $26_b$, the marker image $89_d$ of the second correction marker $26_d$ included in the projection image $84_2$, and the reference position of the second correction marker $26_d$.

Then, in Step S204, the first tomographic image generation unit 66 generates the first tomographic image $86_1$ on the basis of the positional deviation amount derived in Step S202. As described above, the first tomographic image generation unit 66 according to this embodiment generates a plurality of first tomographic images $86_1$ including a part of the object with the first slice thickness from a plurality of projection images $84_1$ to $84_9$ obtained by the tomosynthesis imaging in the first irradiation angle range $AR_1$ among the projection images included in the projection image group acquired in Step S200, using the position of the focus of each of the radiation tubes $27_1$ to $27_9$ whose positional deviation amount has been corrected.

Then, in Step S206, the first composite two-dimensional image generation unit 68 generates the first composite two-dimensional image. As described above, the first composite two-dimensional image generation unit 68 according to this embodiment combines at least some of the plurality of first tomographic images $86_1$ generated in Step S204 to generate the first composite two-dimensional image.

Then, in Step S208, the second tomographic image generation unit 70 generates the second tomographic image $86_2$ on the basis of the positional deviation amount derived in Step S202. As described above, the second tomographic image generation unit 70 according to this embodiment generates a plurality of second tomographic images $86_2$ including the entire object with the second slice thickness from a plurality of projection images $84_4$ to $84_6$ obtained by the tomosynthesis imaging in the second irradiation angle range $AR_2$ among the projection images included in the projection image group acquired in Step S200, using the position of the focus of each of the radiation tubes $27_4$ to $27_6$ whose positional deviation amount has been corrected.

Then, in Step S210, the second composite two-dimensional image generation unit 72 generates the second composite two-dimensional image. As described above, the second composite two-dimensional image generation unit 72 according to this embodiment combines at least some of the plurality of second tomographic images $86_2$ generated in Step S208 to generate the second composite two-dimensional image.

Then, in Step S212, the display control unit 74 displays various radiographic images. Specifically, the display control unit 74 performs control to display the plurality of first tomographic images $86_1$ generated in Step S204, the first composite two-dimensional image generated in Step S206, the plurality of second tomographic images $86_2$ generated in Step S208, and the second composite two-dimensional image generated in Step S210 on the display unit 58.

Figure 12A:
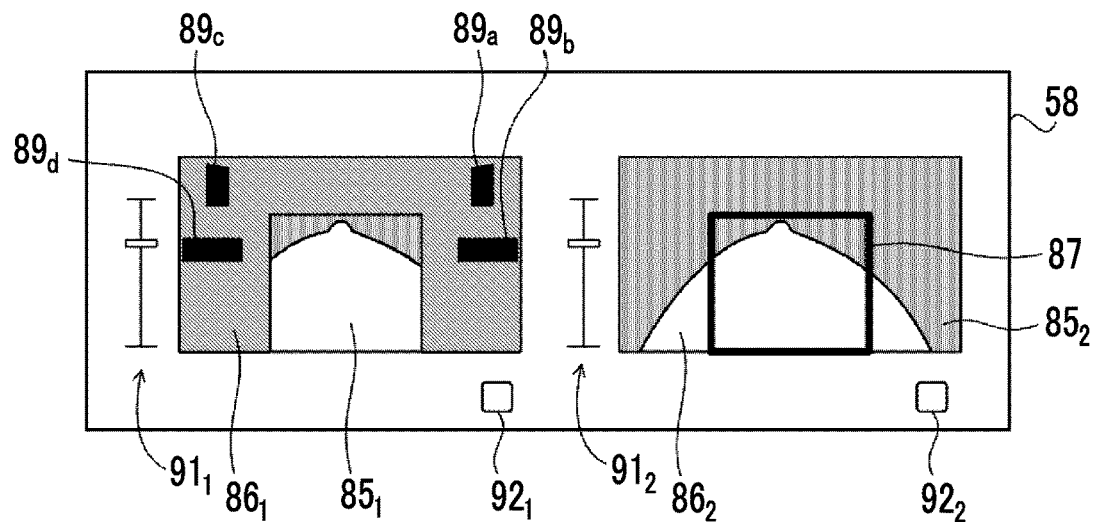
FIG. 12A is a diagram illustrating an example of a state in which a first tomographic image and a second tomographic image are displayed on a display unit.

For example, first, the display control unit 74 according to this embodiment displays the first tomographic image $86_1$ and the second tomographic image $86_2$ side by side on the display unit 58. FIG. 12A illustrates an example of a state in which the first tomographic image $86_1$ and the second tomographic image $86_2$ are displayed on the display unit 58. As illustrated in FIG. 12A, one first tomographic image $86_1$ and a slider bar $91_1$ are displayed on the display unit 58. In a case in which the user operates the operation unit 56 to move a bar of the slider bar $91_1$ along a slider, the first tomographic image $86_1$ having a height corresponding to the position of the bar is displayed on the display unit 58. The marker images $89_a$, $89_b$, $89_c$, and $89_d$ are included in the projection images $84_1$ and $84_9$ used to reconstruct the first tomographic image $86_1$. Therefore, as illustrated in FIG. 12A, the marker images $89_a$, $89_b$, $89_c$, and $89_d$ are included in the first tomographic image $86_1$. All of the marker images $89_a$, $89_b$, $89_c$, and $89_d$ are included in the first tomographic image $86_1$. Therefore, even in a case in which the position of the bar of the slider bar $91_1$ is changed, the marker images $89_a$, $89_b$, $89_c$, and $89_d$ are included in the first tomographic image $86_1$ displayed on the display unit 58.

In addition, one second tomographic image $86_2$ and a slider bar $91_2$ are displayed on the display unit 58. In a case in which the user operates the operation unit 56 to move a bar of the slider bar $91_2$ along a slider, the second tomographic image $86_2$ having a height corresponding to the position of the bar is displayed on the display unit 58. The marker images $89_a$, $89_b$, $89_c$, and $89_d$ are not included in the projection images $84_4$ to $84_6$ used to reconstruct the second tomographic image $86_2$. Therefore, as illustrated in FIG. 12A, the marker images $89_a$, $89_b$, $89_c$, and $89_d$ are not included in the second tomographic image $86_2$. In addition, the display control unit 74 according to this embodiment performs control to align the tomographic planes of the first tomographic image $86_1$ and the second tomographic image $86_2$ displayed on the display unit 58. In other words, the display control unit 74 performs control to align the heights of the first tomographic image $86_1$ and the second tomographic image $86_2$ displayed on the display unit 58. Therefore, in a case in which the user operates either the slider bar $91_1$ or the slider bar $91_2$ to change the height of either the first tomographic image $86_1$ or the second tomographic image $86_2$ displayed on the display unit 58, the height of the other of the first tomographic image $86_1$ and the second tomographic image $86_2$ displayed on the display unit 58 is also changed. Further, unlike this embodiment, the tomographic planes of the first tomographic image $86_1$ and the second tomographic image $86_2$ displayed on the display unit 58 may be different from each other, or a configuration that enables the user to switch whether or not to align the tomographic planes may be used.

Furthermore, as illustrated in FIG. 12A, in a case in which the first tomographic image $86_1$ is displayed, the display control unit 74 according to this embodiment displays reconstructed region information 87 indicating the reconstructed region $85_1$ of the first tomographic image $86_1$ so as to be superimposed on the first tomographic image $86_1$. This display of the reconstructed region information 87 indicating the reconstructed region $85_1$ on the first tomographic image $86_1$ makes it easy for the user to compare the first tomographic image $86_1$ with the second tomographic image $86_2$.

Figure 12B:
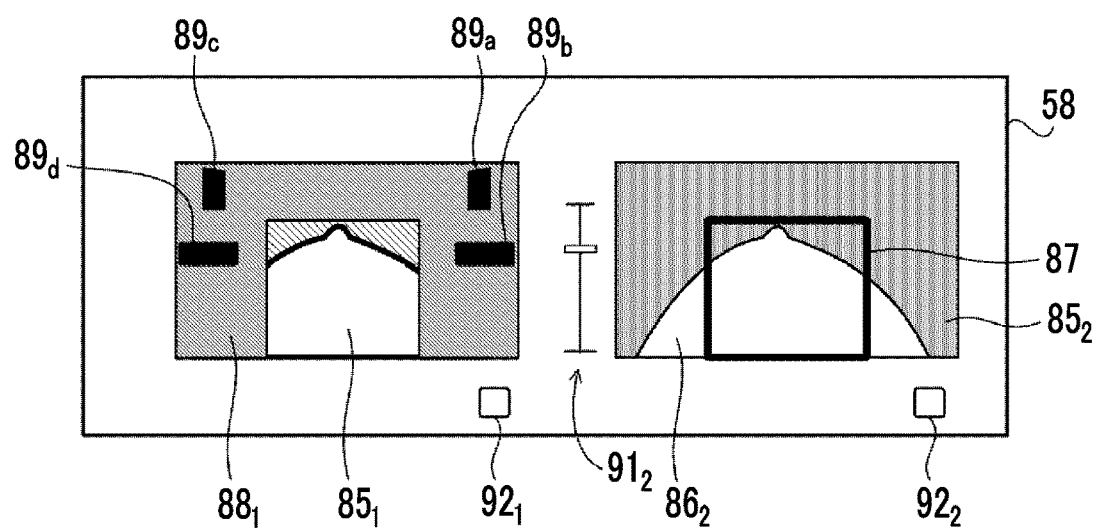
FIG. 12B is a diagram illustrating an example of a state in which a first composite two-dimensional image and the second tomographic image are displayed on the display unit.

Further, as illustrated in FIG. 12A, the display control unit 74 according to this embodiment displays switching buttons $92_1$ and $92_2$ on the display unit 58. In a case in which the operation of the switching button $92_1$ by the user through the operation unit 56 is received, the display control unit 74 performs control to switch the radiographic image displayed on the display unit 58 from one of the first tomographic image $86_1$ and a first composite two-dimensional image $88_1$ to the other. In a case in which the user operates the switching button $92_1$ in the state illustrated in FIG. 12A, the first composite two-dimensional image $88_1$ is displayed on the display unit 58 instead of the first tomographic image $86_1$, as illustrated in FIG. 12B. As illustrated in FIG. 12B, the marker images $89_a$, $89_b$, $89_c$, and $89_d$ are included in the first tomographic image $86_1$ used to generate the first composite two-dimensional image $88_1$. Therefore, as illustrated in FIG. 12B, the marker images $89_a$, $89_b$, $89_c$, and $89_d$ are included in the first composite two-dimensional image $88_1$.

Figure 12C:
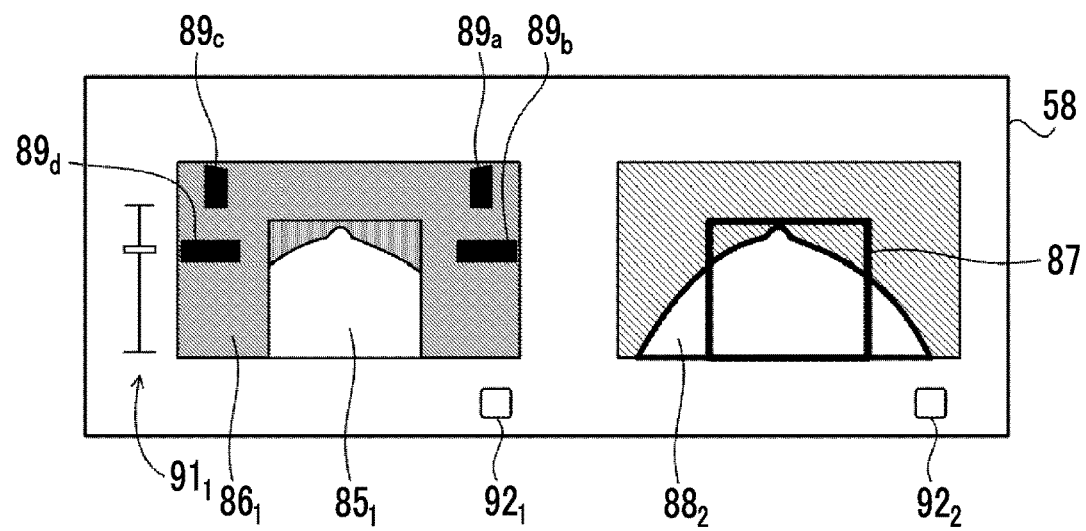
FIG. 12C is a diagram illustrating an example of a state in which the first tomographic image and a second composite two-dimensional image are displayed on the display unit.

On the other hand, in a case in which the operation of the switching button $92_2$ by the user through the operation unit 56 is received, the display control unit 74 performs control to switch the radiographic image displayed on the display unit 58 from one of the second tomographic image $86_2$ and a second composite two-dimensional image $88_2$ to the other. In a case in which the user operates the switching button $92_2$ in the state illustrated in FIG. 12A, the second composite two-dimensional image $88_2$ is displayed on the display unit 58 instead of the second tomographic image $86_2$, as illustrated in FIG. 12C. The marker images $89_a$, $89_b$, $89_c$, and $89_d$ are not included in the second tomographic image $86_2$ used to reconstruct the second composite two-dimensional image $88_2$. Therefore, as illustrated in FIG. 12C, the marker images $89_a$, $89_b$, $89_c$, and $89_d$ are not included in the second composite two-dimensional image $88_2$. Further, in the example illustrated in FIG. 12C, the reconstructed region information 87 is displayed on the second composite two-dimensional image $88_2$. This display of the reconstructed region information 87 on the second composite two-dimensional image $88_2$ makes it easy for the user to compare the first tomographic image $86_1$ or the first composite two-dimensional image $88_1$ with the second composite two-dimensional image $88_2$.

In a case in which the process in Step S212 ends in this way, the image processing illustrated in FIG. 11 ends.

Modification Example 1

The aspect in which the mammography apparatus 10 comprises the plurality of radiation tubes 27 provided at the plurality of irradiation positions 80 has been described above. In contrast, in this modification example, an aspect in which the mammography apparatus 10 comprises the radiation tubes 27 whose number is smaller than the number of irradiation positions 80 will be described. As an example of this case, in this modification example, an aspect in which the mammography apparatus 10 comprises one radiation tube 27 will be described.

Figure 13:
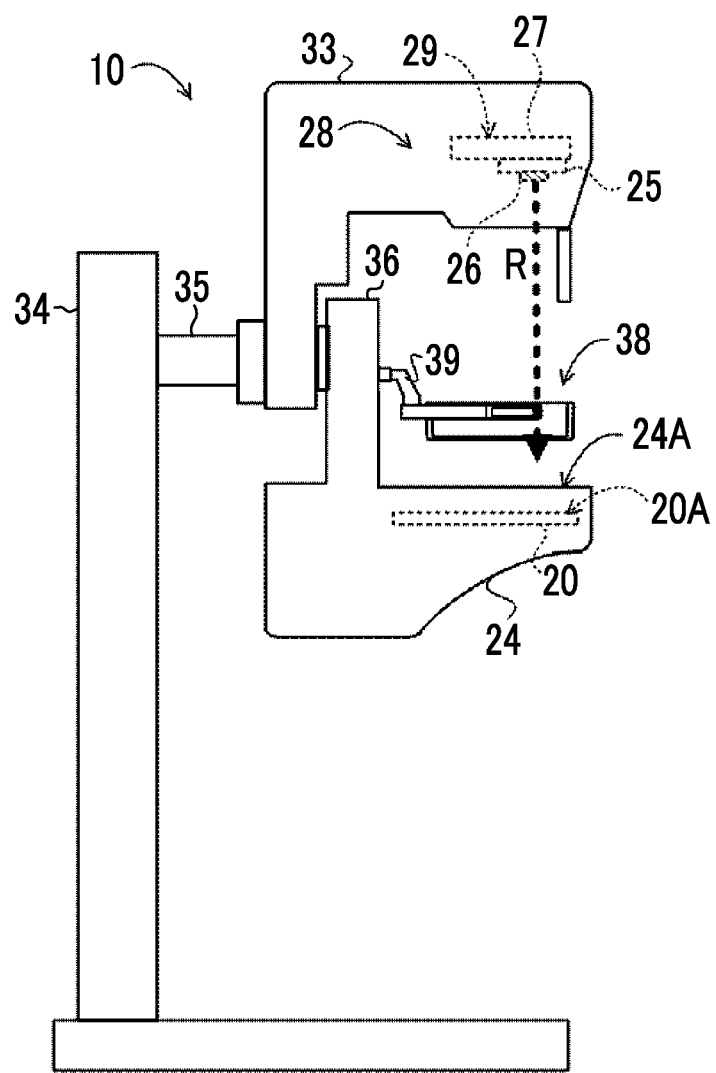
FIG. 13 is a side view illustrating an example of a mammography apparatus according to a modification example.

FIG. 13 is a side view illustrating an example of a mammography apparatus 10 according to this modification example. As illustrated in FIG. 13, in the mammography apparatus 10 according to this modification example, the compression unit 36 and the imaging table 24 are integrated, and the arm portion 33 and the compression unit 36 are held by the base 34 through the shaft portion 35. The arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between the transmission and non-transmission of the power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this modification example, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

As illustrated in FIG. 13, the radiation emitting unit 28 of the mammography apparatus 10 according to this modification example includes a radiation source 29 having one radiation tube 27 and a collimator 25 that is provided so as to correspond to the radiation tube 27. Further, the collimator 25 is provided with a correction marker 26.

Figure 14:
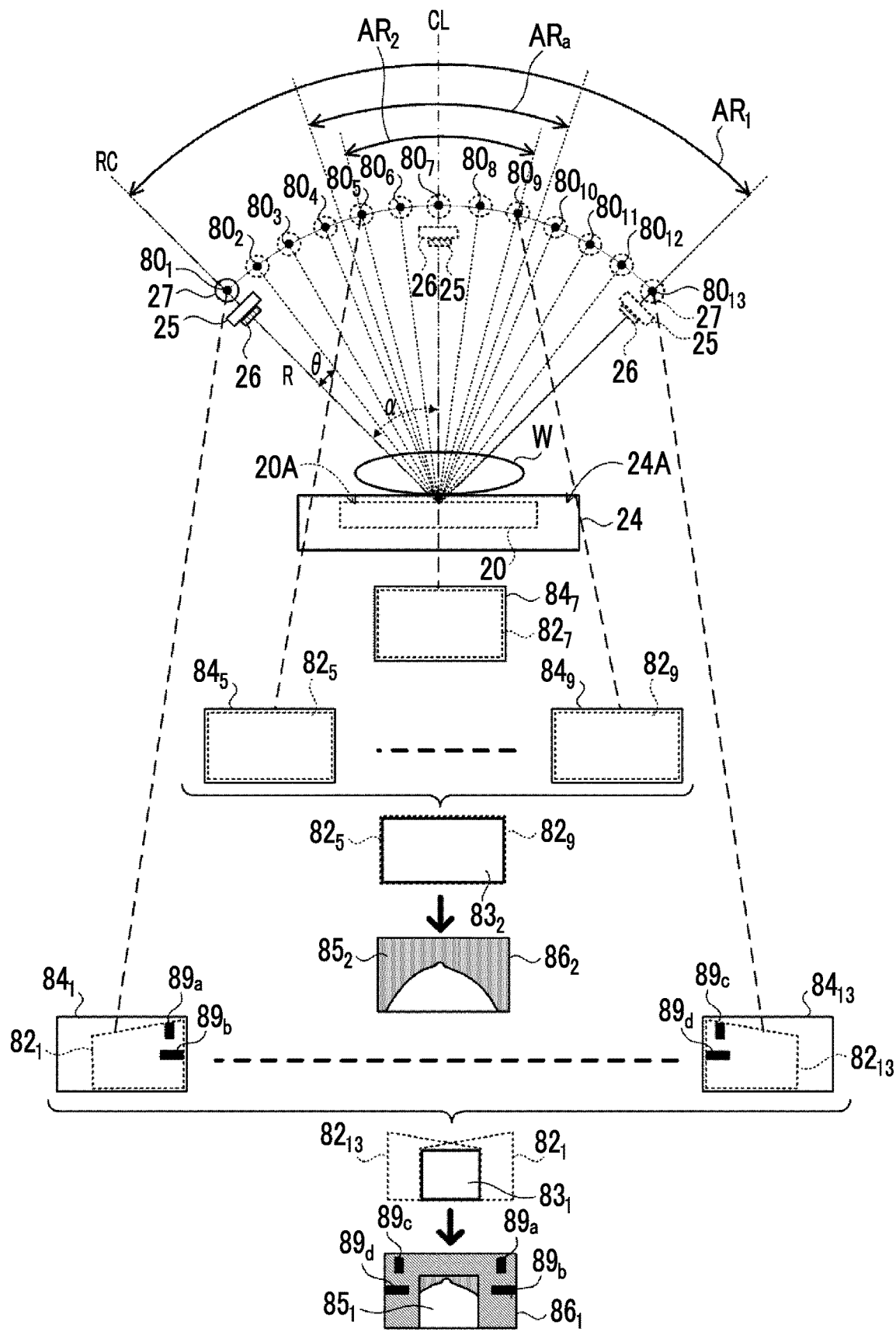
FIG. 14 is a diagram illustrating an example of tomosynthesis imaging in the mammography apparatus according to the modification example.

In a case in which the tomosynthesis imaging is performed in the mammography apparatus 10 according to this modification example illustrated in FIG. 13, the radiation tube 27, the collimator 25, and the correction marker 26 are sequentially moved to each of a plurality of irradiation positions having different irradiation angles by the rotation of the arm portion 33. FIG. 14 is a diagram illustrating an example of the tomosynthesis imaging by the mammography apparatus 10 according to this modification example. In addition, the compression plate 38 is not illustrated in FIG. 14. In this modification example, as illustrated in FIG. 14, the radiation tube 27 is moved to the irradiation positions $80_k$ (k=1, 2, . . . , the maximum value is 13 in FIG. 14) having different irradiation angles that are arranged at an interval of a predetermined angle θ. At each of the irradiation positions $80_k$, the radiation source 29 emits the radiation R to the breast W in response to an instruction from the console 12, and the radiation detector 20 captures a radiographic image. In the radiography system 1, in a case in which the tomosynthesis imaging that moves the radiation source 29 to each of the irradiation positions $80_k$ and captures radiographic images at each of the irradiation positions $80_k$ is performed, 13 radiographic images are obtained in the example illustrated in FIG. 14.

In the case of the first irradiation angle range $AR_1$ wider than the overall imaging irradiation angle range $AR_a$, a partial region $83_1$ common to object regions $82_1$ to $82_{13}$ included in projection images $84_1$ to $84_{13}$ obtained at each of the irradiation positions $80_1$ to $80_{13}$ corresponds to a reconstructed region $85_1$ in a case in which a first tomographic image $86_1$ is generated. The partial region $83_1$, that is, the reconstructed region $85_1$ is smaller than the object regions $82_1$ to $82_{13}$ included in the projection images $84_1$ to $84_{13}$. Therefore, in this modification example, the first tomographic image $86_1$ is an image in which a part of the object is included. For example, FIG. 14 illustrates the first tomographic image $86_1$ in which a part of the breast W, which is the object, is included.

Since the first irradiation angle range $AR_1$ is wider than the overall imaging irradiation angle range $AR_a$, the first tomographic image $86_1$ generated using a plurality of first projection images $84_1$ to $84_{13}$ obtained by the tomosynthesis imaging in the first irradiation angle range $AR_1$ is a high-resolution image.

On the other hand, in a case in which the irradiation angle range is equal to or narrower than the overall imaging irradiation angle range $AR_a$, the reconstructed region 85 in the tomographic image 86 is equivalent to the object region $82_7$. Therefore, the tomographic image 86 is an image in which the entire object is included.

In a case in which the irradiation angle range is the second irradiation angle range $AR_2$, a partial region $83_2$ common to the object regions $82_5$ to $82_9$ included in the projection images $84_5$ to $84_9$ obtained at each of the irradiation positions $80_5$ to $80_9$ corresponds to a reconstructed region $85_2$ in a case in which a second tomographic image $86_2$ is generated. The partial region $83_2$, that is, the reconstructed region $85_2$ is equivalent to the object regions $82_5$ to $82_9$ included in the projection images $84_5$ to $84_9$. Therefore, in this modification example, the second tomographic image $86_2$ is an image in which the entire object is included. For example, FIG. 14 illustrates the second tomographic image $86_2$ in which the entire breast W, which is the object, is included.

Figure 15:
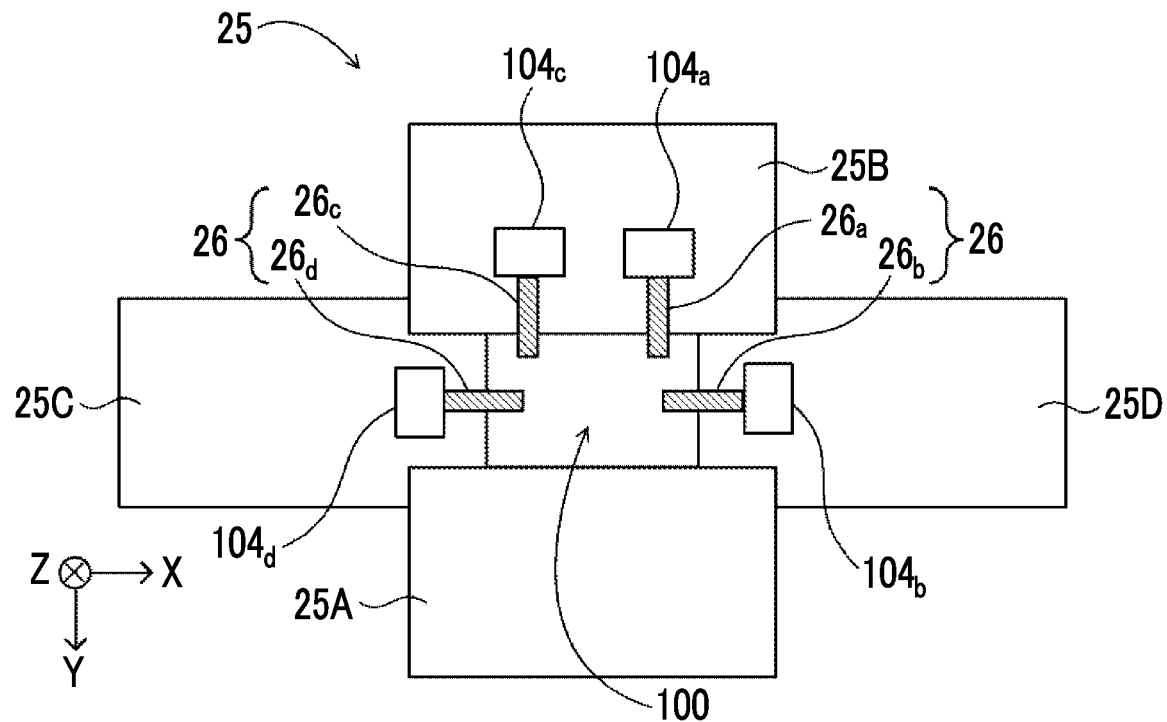
FIG. 15 is a plan view illustrating an example of a correction marker provided in a collimator in the modification example as viewed from the imaging table.

Further, as illustrated in FIG. 15, the collimator 25 that is provided so as to correspond to the radiation tube 27 is provided with a correction marker 26. FIG. 15 is a plan view illustrating an example of the correction marker 26 provided in the collimator 25 as viewed from the imaging table 24. As illustrated in FIG. 15, the correction marker 26 includes first correction markers $26_a$ and $26_c$ and second correction markers $26_b$ and $26_d$. The correction marker 26 is provided such that it can be moved into the irradiation path of the radiation R that has passed through the opening portion 100 of the collimator 25 and can be moved out of the irradiation path. Specifically, the first correction marker $26_a$ is provided on the blade 25B. The first correction marker $26_a$ can be moved into the opening portion 100 and can be moved out of the opening portion 100 by a marker movement mechanism $104_a$. FIG. 15 illustrates a state in which the first correction marker $26_a$ has been moved into the opening portion 100 by the marker movement mechanism 104a. The second correction marker $26_b$ is provided on the blade 25D. The second correction marker $26_b$ can be moved into the opening portion 100 and can be moved out of the opening portion 100 by a marker movement mechanism $104_b$. FIG. 15 illustrates a state in which the second correction marker $26_b$ has been moved into the opening portion 100 by the marker movement mechanism $104_b$. The first correction marker $26_c$ is provided on the blade 25B. The first correction marker $26_c$ can be moved into the opening portion 100 and can be moved out of the opening portion 100 by a marker movement mechanism $104_c$. FIG. 15 illustrates a state in which the first correction marker $26_c$ has been moved into the opening portion 100 by the marker movement mechanism $104_c$. Further, the second correction marker $26_d$ is provided on the blade $25_c$. The second correction marker $26_d$ can be moved into the opening portion 100 and can be moved out of the opening portion 100 by a marker movement mechanism $104_d$. FIG. 15 illustrates a state in which the second correction marker $26_d$ has been moved into the opening portion 100 by the marker movement mechanism $104_d$.

In a case in which the correction marker 26 is moved into the irradiation path of the radiation R, in other words, in a case in which the correction marker 26 is moved into the opening portion 100, the marker image 89 of the correction marker 26 is included in the projection image 84. Therefore, as illustrated in FIG. 15, in a case in which the radiation emitting unit 28 is moved to each irradiation position 80 with the correction marker 26 moved into the opening portion 100, the marker image 89 of the correction marker 26 is included in the projection image 84. For example, in the example illustrated in FIG. 14, at the irradiation positions $80_5$ to $80_9$ corresponding to the overall imaging irradiation angle range $AR_a$, the marker image 89 is included in the projection images $84_5$ to $84_9$ in a state in which the correction marker 26 has been moved into the opening portion 100. Therefore, in this modification example, the correction marker 26 can be moved into the irradiation path in a case in which the radiation emitting unit 28, specifically, the radiation tube 27 is located at least at the irradiation positions 80 outside the overall imaging irradiation angle range $AR_a$ and can be moved out of the irradiation path in a case in which the radiation tube 27 is located at an irradiation position other than the irradiation positions 80 outside the overall imaging irradiation angle range $AR_a$.

Figure 16A:
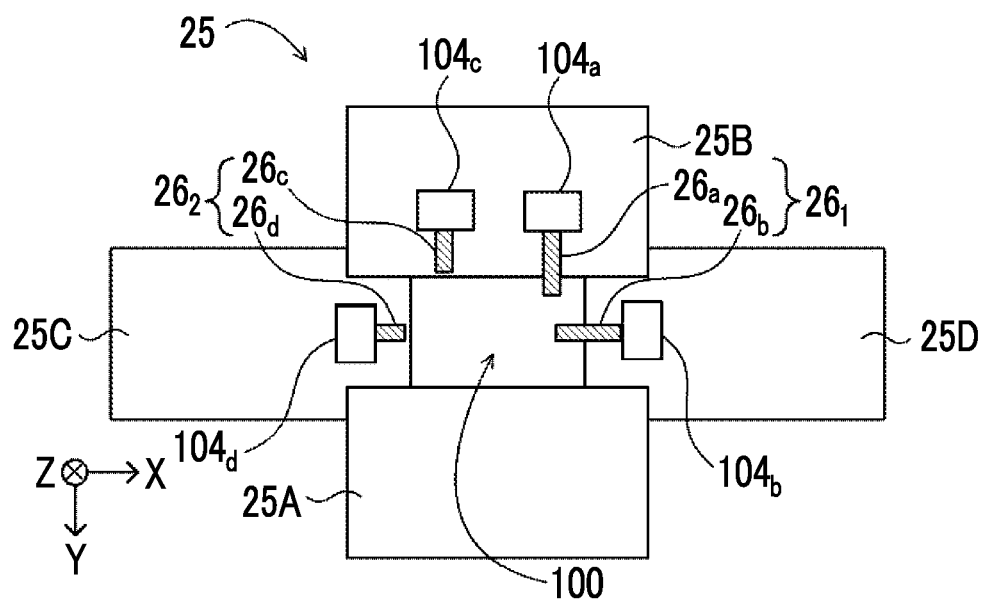
FIG. 16A is a plan view illustrating an example of the correction marker provided in the collimator in the modification example as viewed from the imaging table.

That is, in this modification example, the correction marker 26 is moved into the irradiation path of the radiation R or is moved out of the irradiation path at each irradiation position 80 such that the marker image 89 is included in a region other than the reconstructed region 85 in the projection image 84. Specifically, in a case in which the radiation tube 27 is located at the irradiation position $80_1$, as illustrated in FIG. 16A, the first correction marker $26_a$ and the second correction marker $26_b$ are moved into the opening portion 100 by the marker movement mechanisms $104_a$ and $104_b$, respectively. Further, as illustrated in FIG. 16A, the first correction marker $26_c$ and the second correction marker $26_d$ are moved out of the opening portion 100 by the marker movement mechanisms $104_c$ and $104_d$, respectively. Therefore, as illustrated in FIG. 14, the marker image $89_a$ of the first correction marker $26_a$ and the marker image $89_b$ of the second correction marker $26_b$ are included in the projection image $84_1$ obtained at the irradiation position $80_1$.

Figure 16B:
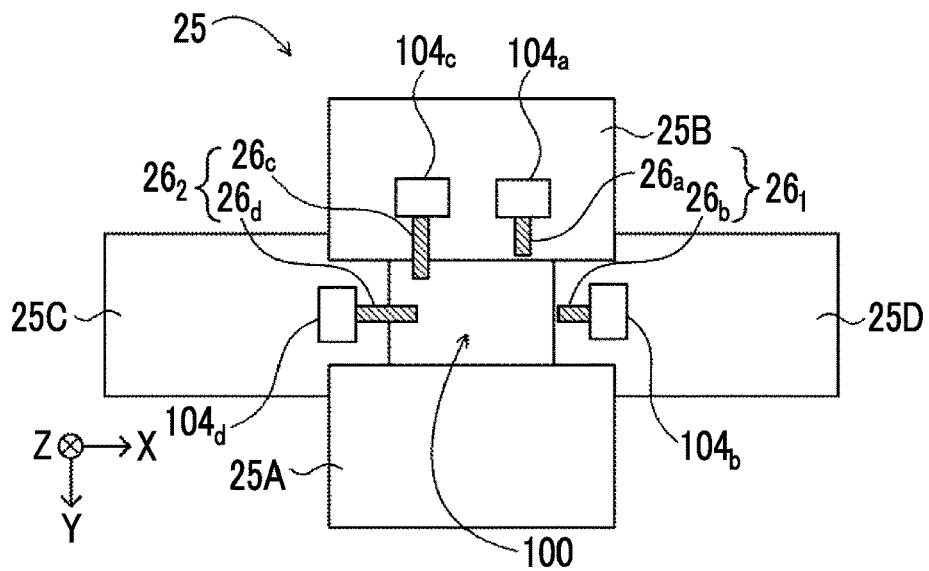
FIG. 16B is a plan view illustrating an example of the correction marker provided in the collimator in the modification example as viewed from the imaging table.

In addition, as illustrated in FIG. 16B, in a case in which the radiation tube 27 is located at the irradiation position $80_{13}$, the first correction marker $26_a$ and the second correction marker $26_b$ are moved out of the opening portion 100 by the marker movement mechanisms $104_a$ and $104_b$, respectively. Further, as illustrated in FIG. 16B, the first correction marker $26_c$ and the second correction marker $26_d$ are moved into the opening portion 100 by the marker movement mechanisms $104_c$ and $104_d$, respectively. Therefore, as illustrated in FIG. 14, the marker image $89_c$ of the first correction marker $26_c$ and the marker image $89_d$ of the second correction marker $26_d$ are included in the projection image $84_{13}$ obtained at the irradiation position $80_{13}$.

Figure 16C:
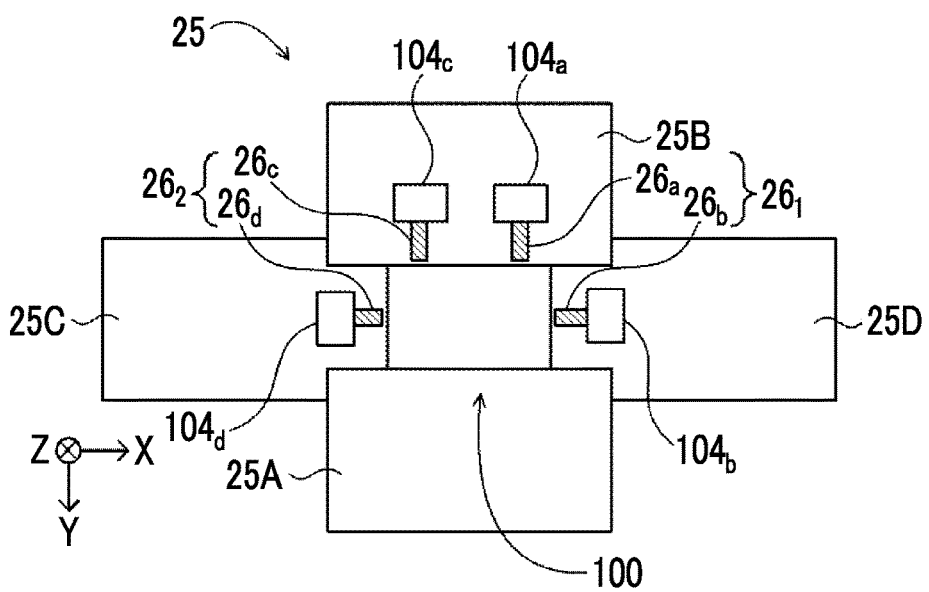
FIG. 16C is a plan view illustrating an example of the correction marker provided in the collimator in the modification example as viewed from the imaging table.

In addition, as illustrated in FIG. 16C, in a case in which the radiation tube 27 is located at the irradiation positions $80_2$ to $80_{12}$, the first correction markers $26_a$ and $26_c$ and the second correction markers $26_b$ and $26_d$ are moved out of the opening portion 100 by the marker movement mechanisms $104_a$, $104_b$, $104_c$, and $104_d$, respectively. Therefore, as illustrated in FIG. 14, none of the marker images $89_a$ to $89_d$ are included in the projection images $84_2$ to $84_{12}$ obtained at the irradiation positions $80_2$ to $80_{12}$.

As described above, in the first tomographic image $86_1$, the marker images $89_a$ to $89_d$ are included in a region other than the reconstructed region $85_1$. Further, none of the marker images $89_a$ to $89_d$ are included in the second tomographic image $86_2$.

In addition, the specific configuration of the marker movement mechanism 104 is not particularly limited as long as it can move the correction marker 26 into the irradiation path of the radiation R and move the correction marker 26 out of the irradiation path. For example, a solenoid can be applied as the marker movement mechanism 104.

Figure 17:
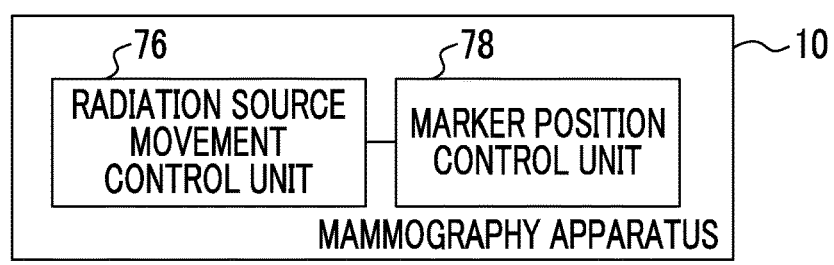
FIG. 17 is a functional block diagram illustrating an example of the functions of the mammography apparatuses according to the modification example.

As described above, the mammography apparatus 10 according to this modification example performs control to move the correction marker 26 into the irradiation path or to move the correction marker 26 out of the irradiation path according to the irradiation position 80 where the radiation tube 27 is located. Therefore, the mammography apparatus 10 according to this modification example has a function of controlling the movement of the correction marker 26 into or out of the irradiation path in the tomosynthesis imaging. FIG. 17 is a functional block diagram illustrating an example of a configuration related to the function of controlling the movement of the correction marker 26 into or out of the irradiation path in the mammography apparatus 10 according to this modification example. As illustrated in FIG. 17, the mammography apparatus 10 according to this modification example comprises a radiation source movement control unit 76 and a marker position control unit 78. As an example, in the mammography apparatus 10 according to this modification, the CPU 40A of the control unit 40 executes the imaging program 41 stored in the ROM 40B to function as the radiation source movement control unit 76 and the marker position control unit 78.

The radiation source movement control unit 76 has a function of moving the radiation source 29 to each irradiation position 80 to move the radiation tube 27 to each irradiation position 80 and directing the radiation tube 27 to emit the radiation R at the moved irradiation position 80. The radiation source movement control unit 76 has a function of moving the radiation tube 27 of the radiation source 29 to each of the plurality of irradiation positions 80 in a case in which the tomosynthesis imaging is performed as described above. Specifically, the radiation source movement control unit 76 rotates the arm portion 33 with respect to the imaging table 24 to move the radiation source 29 to each of the plurality of irradiation positions 80. The radiation source movement control unit 76 according to this modification example is provided in the arm portion 33.

The marker position control unit 78 has a function of performing control such that the correction marker 26 is moved to a position in the irradiation path of the radiation R or a position out of the irradiation path. Specifically, the radiation source movement control unit 76 performs control such that each of the correction markers $26_a$ to $26_d$ is moved to a position in the opening portion 100 or a position out of the opening portion 100 by the marker movement mechanisms $104_a$ to $104_d$ according to the irradiation position 80 as described above.

Figure 18:
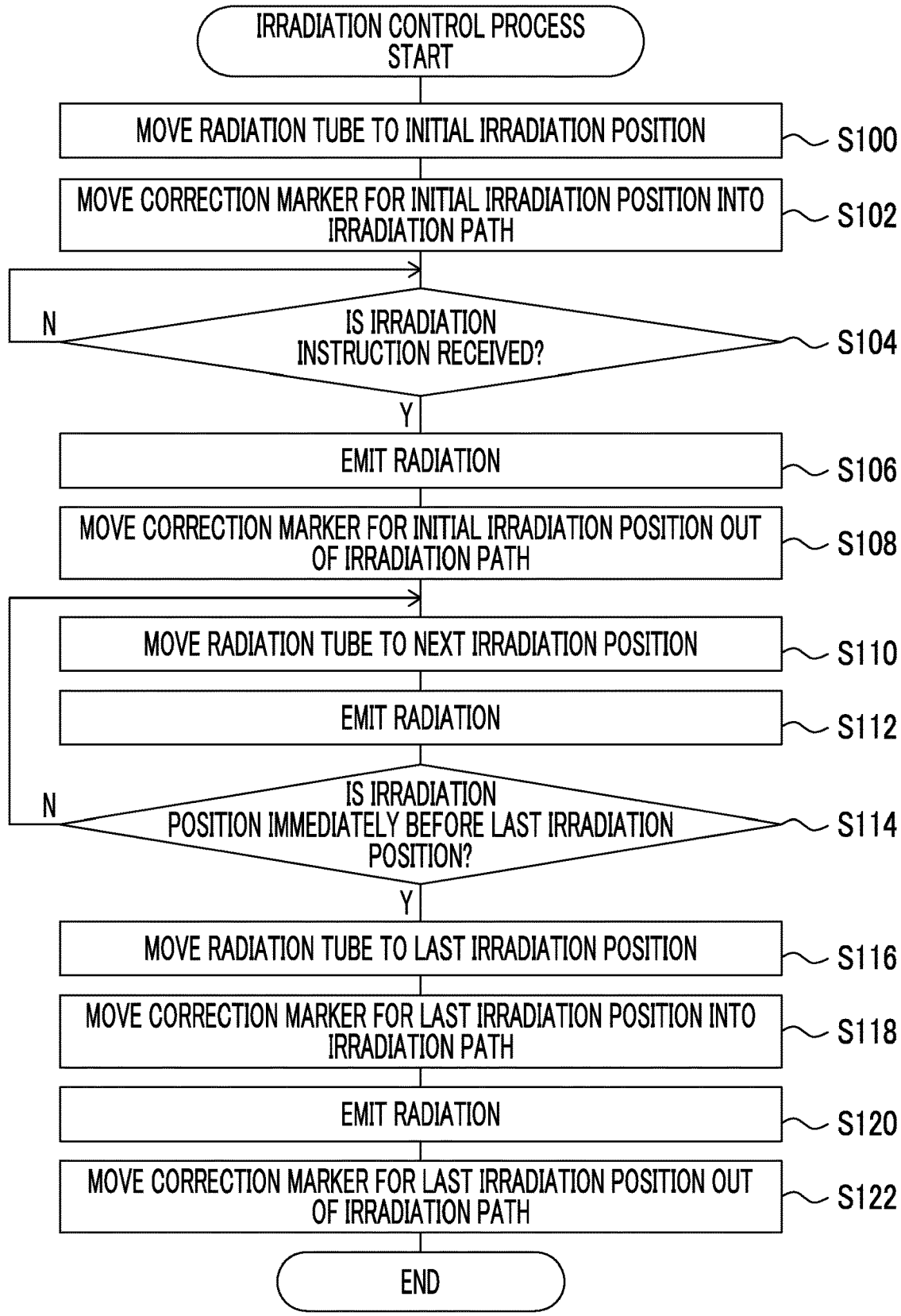
FIG. 18 is a flowchart illustrating an example of the flow of an irradiation control process by the mammography apparatus according to the modification example.

Next, the operation of the mammography apparatus 10 in the tomosynthesis imaging will be described with reference to the drawings. In a case in which the tomosynthesis imaging performed in Step S10 of FIG. 10, the mammography apparatus 10 performs an irradiation control process illustrated in FIG. 18. FIG. 18 is a flowchart illustrating an example of the flow of the irradiation control process by the mammography apparatus 10 according to this modification example. In the mammography apparatus 10 according to this modification example, for example, the CPU 40A of the control unit 40 executes the imaging program 41 stored in the ROM 40B to perform the irradiation control process whose example is illustrated in FIG. 18. Further, in a case in which the tomosynthesis imaging is started, the correction marker 26 is located at the position out of the irradiation path of the radiation R.

In Step S100 of FIG. 18, the radiation source movement control unit 76 moves the radiation tube 27 to the initial irradiation position 80 in the tomosynthesis imaging. In the example illustrated in FIG. 14, the radiation tube 27 is moved to the irradiation position $80_1$.

Then, in Step S102, the marker position control unit 78 performs control to move the correction marker 26 for the initial irradiation position 80 to the position in the irradiation path of the radiation R. As described above, as illustrated in FIG. 16A, the marker position control unit 78 performs control such that the first correction marker $26_a$ is moved to the position in the opening portion 100 by the marker movement mechanism $104_a$. Further, as illustrated in FIG. 16A, the marker position control unit 78 performs control such that the second correction marker $26_b$ is moved to the position in the opening portion 100 by the marker movement mechanism $104_b$.

Then, in Step S104, the radiation source movement control unit 76 determines whether or not an irradiation instruction has been received. As described above, the determination result in Step S104 is "No" until the instruction to emit the radiation R input by the user through the operation unit 56 is received. On the other hand, in a case in which the irradiation instruction has been received, the determination result in Step S104 is "Yes", and the process proceeds to Step S106.

In Step S106, the radiation source movement control unit 76 performs control such that the radiation R is emitted from the radiation tube 27. Therefore, the projection image 84 is captured. As described above, in this modification example, the projection image $84_1$ in which the marker images $89_a$ and $89_b$ are included is captured.

Then, in Step S108, the marker position control unit 78 performs control such that the correction marker 26 for the initial irradiation position 80 is moved to the position out of the irradiation path of the radiation R. As described above, the marker position control unit 78 performs control such that the first correction marker $26_a$ is moved to the position out of the opening portion 100 by the marker movement mechanism $104_a$. Further, the marker position control unit 78 performs control such that the second correction marker $26_b$ is moved to the position out of the opening portion 100 by the marker movement mechanism $104_b$.

Then, in Step S110, the radiation source movement control unit 76 performs control to move the radiation tube 27 to the next irradiation position 80.

Then, in Step S112, the radiation source movement control unit 76 performs control such that the radiation R is emitted from the radiation tube 27. Therefore, the projection image 84 is captured. In this case, since all of the correction markers 26 are located at the position out of the irradiation path of the radiation R, the marker image 89 is not included in the obtained projection image 84.

Then, in Step S114, the radiation source movement control unit 76 determines whether or not the irradiation position 80 is an irradiation position 80 immediately before the last irradiation position. In this modification example, the radiation source movement control unit 76 determines whether or not the irradiation position 80 is the irradiation position $80_{12}$. In a case in which the irradiation position 80 is not the irradiation position $80_{12}$, in other words, in a case in which the irradiation position 80 is any of the irradiation positions $80_2$ to $80_{11}$, the determination result in Step S114 is "No", and the process returns to Step S110. Then, Steps S110 and S112 are repeated. On the other hand, in a case in which the irradiation position 80 is the irradiation position $80_{12}$, the determination result in Step S114 is "Yes", and the process proceeds to Step S116.

In Step S116, the radiation source movement control unit 76 moves the radiation tube 27 to the last irradiation position 80 in the tomosynthesis imaging. In the example illustrated in FIG. 14, the radiation tube 27 is moved to the irradiation position $80_{13}$.

Then, in Step S118, the marker position control unit 78 performs control to move the correction marker 26 for the last irradiation position 80 to the position in the irradiation path of the radiation R. As described above, as illustrated in FIG. 16B, the marker position control unit 78 performs control such that the first correction marker $26_c$ is moved to the position in the opening portion 100 by the marker movement mechanism $104_c$. In addition, as illustrated in FIG. 16B, the marker position control unit 78 performs control such that the second correction marker $26_d$ is moved to the position in the opening portion 100 by the marker movement mechanism $104_d$.

Then, in Step S120, the radiation source movement control unit 76 performs control such that the radiation R is emitted from the radiation tube 27. Therefore, the projection image 84 is captured. As described above, in this modification example, the projection image $84_{13}$ in which the marker images $89_c$ and $89_d$ are included is captured.

Then, in Step S122, the marker position control unit 78 performs control to move the correction marker 26 for the last irradiation position 80 to the position out of the irradiation path of the radiation R. As described above, the marker position control unit 78 performs control such that the first correction marker $26_c$ is moved to the position out of the opening portion 100 by the marker movement mechanism $104_c$. Further, the marker position control unit 78 performs control such that the second correction marker $26_d$ is moved to the position out of the opening portion 100 by the marker movement mechanism $104_d$. In a case in which the process in Step S122 ends, the irradiation control process illustrated in FIG. 18 ends.

In this way, the console 12 generates the first tomographic image $86_1$, the second tomographic image $86_2$, the first composite two-dimensional image $88_1$, and the second composite two-dimensional image $88_2$ using the captured projection images $84_1$ to $84_{13}$ as described above.

Therefore, even in the mammography apparatus 10 according to this modification example that moves the radiation emitting unit 28 to move the radiation tube 27 to each irradiation position 80, it is possible to correct the position of the focus of the radiation tube 27 at each irradiation position 80 on the basis of the position of the marker image 89 of the correction marker 26 included in the projection image 84 and the reference position of the marker image 89.

As described above, the radiography system 1 according to the above-described embodiment comprises: the radiation emitting unit 28 including the radiation tube 27 that generates the radiation R from a focus and the collimator 25 that is provided so as to correspond to the radiation tube 27 and limits the irradiation field 102 of the radiation R; the radiation detector 20 that receives the radiation R, which has been emitted from the radiation emitting unit 28 and transmitted through the object, to detect the projection image 84 of the object; and the mammography apparatus 10 that irradiates the object with the radiation R emitted from the radiation emitting unit 28 at a plurality of irradiation positions 80 having different irradiation angles and controls the tomosynthesis imaging. Further, the radiography system 1 comprises the correction marker 26 that is used to obtain the marker image 89 included in at least one of a plurality of projection images 84 obtained by the tomosynthesis imaging, is provided in the irradiation path of the radiation in the radiation emitting unit 28, and is disposed at the position where the marker image 89 is included in a region other than the reconstructed region 85 in the projection image 84, the reconstructed region 85 being a region used in a case in which the tomographic image is reconstructed from the plurality of projection images 84 among the regions included in the plurality of projection images 84.

As described above, in the radiography system 1, the marker image 89 of the correction marker 26 is included in the region other than the reconstructed region 85 in the projection image 84. Therefore, in the tomographic image obtained by reconstructing the projection images 84, the marker image 89 is included at a position outside the reconstructed region. As a result, according to the radiography system 1 of the above-described embodiment, it is possible to prevent the marker image 89 of the correction marker 26 from being included in the reconstructed region of the tomographic image obtained by reconstructing a plurality of projection images 84. The reconstructed region 85 is a region used by the user for image interpretation, such as the diagnosis of an object. According to the radiography system 1 of the above-described embodiment, the marker image 89 is not included in the reconstructed region. Therefore, even in a case in which the marker image 89 is included in the tomographic image, it does not hinder image interpretation by the user.

Further, in the above-described embodiment, the tomosynthesis imaging in the first irradiation angle range $AR_1$ and the tomosynthesis imaging in the second irradiation angle range $AR_2$ can be performed by one tomosynthesis imaging operation. Therefore, even in an aspect in which the tomosynthesis imaging in the first irradiation angle range $AR_1$ and the tomosynthesis imaging in the second irradiation angle range $AR_2$ are performed separately, that is, an aspect in which the tomosynthesis imaging is performed twice, it is possible to reduce the time until two tomosynthesis imaging operations end. In addition, the movement of the object can be suppressed by suppressing the time until imaging ends.

In this embodiment, "one tomosynthesis imaging operation" means at least tomosynthesis imaging that is performed with the breast compressed by the compression plate 38. Therefore, the one tomosynthesis imaging operation also includes a case in which, after the tomosynthesis imaging in the first irradiation angle range $AR_1$ is performed with the breast compressed by the compression plate 38, the tomosynthesis imaging in the second irradiation angle range $AR_2$ is performed with the breast compressed by the compression plate 38. Alternatively, the "one tomosynthesis imaging" means tomosynthesis imaging that is performed from the start of the capture of the projection image 84 at the irradiation position 80 defined as a start position to the end of the capture of the projection image 84 at the irradiation position 80 defined as an end position by, for example, the imaging menu.

Further, in the above-described embodiment, the projection images $84_4$ to $84_6$ obtained by the tomosynthesis imaging in the first irradiation angle range $AR_1$ are used as the projection images $84_4$ to $84_6$ obtained by the tomosynthesis imaging in the second irradiation angle range $AR_2$. As described above, the console 12 according to the above-described embodiment uses one projection image 84 to generate the first tomographic image $86_1$ and the second tomographic image $86_2$. Therefore, it is possible to reduce the number of times the projection image 84 is captured in the entire tomosynthesis imaging and to shorten the time related to the entire tomosynthesis imaging until the two types of tomosynthesis imaging end.

In addition, in the above-described embodiment, the aspect in which the marker image 89 of the correction marker 26 is included in the projection images 84 obtained at the irradiation positions 80 at both ends of the first irradiation angle range $AR_1$ has been described. However, the projection image 84 in which the marker image 89 is included is not limited to this aspect. The marker image 89 may be included in a region outside the reconstructed region 85 of the projection image 84. For example, the marker image 89 of the correction marker 26 may be included in the projection image 84 obtained at one of the irradiation positions 80 at both ends of the first irradiation angle range $AR_1$. Further, the marker image 89 of the correction marker 26 may be included in the projection image 84 obtained by any of the outer irradiation positions 80 outside the overall imaging irradiation angle range $AR_a$.

Further, in the above-described embodiment, the aspect in which two types of tomographic images of the first tomographic image $86_1$ and the second tomographic image $86_2$ are generated has been described. However, either the first tomographic image $86_1$ or the second tomographic image $86_2$ may be generated. In addition, in the aspect in which only the second tomographic image $86_2$ is generated, the marker image 89 of the correction marker 26 is not included in the projection image 84 obtained at each irradiation position 80 in the second irradiation angle range $AR_2$. Therefore, the projection image 84 in which the marker image 89 of the correction marker 26 is included is obtained at one or more of the irradiation positions 80 outside the overall imaging irradiation angle range $AR_a$. Then, the second tomographic image generation unit 70 generates the second tomographic image $86_2$ from the projection images 84 on the basis of the positional deviation amount of the focus of the radiation tube 27 at each irradiation position 80 in the second irradiation angle range $AR_2$ which is obtained by the projection images 84 in which the marker image 89 of the correction marker 26 is included. Further, in this case, the projection images 84 in which the marker image 89 is included are not used for reconstruction, which makes it possible to prevent the marker image 89 from being included in the second tomographic image $86_2$. Furthermore, in a case in which the projection image 84 in which the marker image 89 of the correction marker 26 is included is captured, the projection image 84 is not used for image interpretation and suffices for specifying the position of the marker image 89 in the projection image 84. Therefore, the dose of the radiation R can be lower than that for other projection images 84.

Moreover, in the above-described embodiment, the aspect in which the console 12 derives the positional deviation amount of the focus of the radiation tube 27 and generates the first tomographic image $86_1$ and the second tomographic image $86_2$ on the basis of the derived positional deviation amount has been described. However, the console 12 may generate the first tomographic image $86_1$ and the second tomographic image $86_2$ on the basis of the position of the marker image 89 included in the projection image 84 and the reference position of the marker image 89 without deriving the positional deviation amount. For example, in a case in which a correction coefficient for the position of the focus of the radiation tube 27 at each irradiation position 80 is associated with the positional deviation amounts La to Ld between the marker image 89 and the reference image 90 in advance, the first tomographic image $86_1$ and the second tomographic image $86_2$ may be generated on the basis of the position of the focus of the radiation tube 27 corrected using the correction coefficients corresponding to the derived positional deviation amounts La to Ld.

In addition, in the above-described embodiment, the aspect in which the correction markers 26 are provided on the blades 25B to 25D of the collimator 25 has been described. However, the position where the correction marker 26 is provided is not limited to the above-mentioned aspect as long as it is located in the irradiation path of the radiation R emitted from the radiation tube 27.

Further, in the above-described embodiment, the aspect in which the console 12 is an example of the image processing device according to the present disclosure has been described. However, devices other than the console 12 may have the functions of the image processing device according to the present disclosure. In other words, a device, such as the mammography apparatus 10 or an external device, other than the console 12 may have some or all of the functions of the information acquisition unit 60, the image acquisition unit 64, the positional deviation amount derivation unit 65, the first tomographic image generation unit 66, the first composite two-dimensional image generation unit 68, the second tomographic image generation unit 70, the second composite two-dimensional image generation unit 72, and the display control unit 74. Furthermore, for example, the console 12 or an external device other than the mammography apparatus 10 may have some or all of the functions of the radiation source movement control unit 76 and the marker position control unit 78 of the mammography apparatus 10.

In addition, in the above-described embodiment, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

Further, in the above-described embodiment, for example, the following various processors can be used as the hardware structure of processing units performing various processes such as the information acquisition unit 60, the image acquisition unit 64, the positional deviation amount derivation unit 65, the first tomographic image generation unit 66, the first composite two-dimensional image generation unit 68, the second tomographic image generation unit 70, the second composite two-dimensional image generation unit 72, the display control unit 74, the radiation source movement control unit 76, and the marker position control unit 78. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging program 41 is stored (installed) in the ROM 40B in advance, and the imaging control program 51A and the image generation program 51B are stored (installed) in the ROM 50B in advance has been described. However, the present disclosure is not limited thereto. The imaging program 41A, the imaging control program 51A, and the image generation program 51B may be recorded on a recording medium, such as a compact disc read only memory (CD-ROM), a digital versatile disc read only memory (DVD-ROM), or a universal serial bus (USB) memory, and then provided. Further, each of the imaging program 41A, the imaging control program 51A, and the image generation program 51B may be downloaded from an external device through a network.

What is claimed is:

1. A radiography system comprising:
   a radiation emitting unit including a radiation tube that generates radiation from a focus and an irradiation field limiter that is provided so as to correspond to the radiation tube and limits an irradiation field of the radiation;
   a radiation detector that receives the radiation, which has been emitted from the radiation emitting unit and transmitted through an object, to detect a projection image of the object;
   an imaging control device that irradiates the object with the radiation at a plurality of irradiation positions having different irradiation angles and controls tomosynthesis imaging; and
   a correction marker that is used to obtain a marker image included in at least one of a plurality of the projection images obtained by the tomosynthesis imaging, is provided in an irradiation path of the radiation in the radiation emitting unit, and is disposed at a position where the marker image is included in a region other than a reconstructed region in the projection image, the reconstructed region being a region used in a case in which the tomographic image is reconstructed from the plurality of projection images among regions included in the plurality of projection images,
   wherein the tomosynthesis imaging is possible in a first irradiation angle range wider than an overall imaging irradiation angle range which is an irradiation angle range in which an entire tomographic image including an entire object is obtainable in a case in which the tomographic image is reconstructed from the projection images obtained at each of the plurality of irradiation positions, and
   wherein the correction marker is disposed in the irradiation path of the radiation emitted at an outer irradiation position which is outside the overall imaging irradiation angle range in the first irradiation angle range and where a partial tomographic image including only a part of the object is obtained.

2. The radiography system according to claim 1, wherein the correction marker is disposed in the irradiation path of the radiation emitted at two irradiation positions which correspond to both ends of an irradiation angle range among the plurality of irradiation positions.

3. The radiography system according to claim 1, wherein the radiation emitting unit includes a plurality of the radiation tubes.

4. The radiography system according to claim 3, wherein the correction marker is provided in at least one of the irradiation field limiters which are provided so as to correspond to the radiation tubes disposed at the outer irradiation positions.

5. The radiography system according to claim 1, wherein the radiation emitting unit is movable to the plurality of irradiation positions.

6. The radiography system according to claim 5, wherein the correction marker is moved into the irradiation path in a case in which the radiation emitting unit is located at least at the outer irradiation position and is movable out of the irradiation path in a case in which the radiation emitting unit is located at the irradiation position other than the outer irradiation position.

7. The radiography system according to claim 1, further comprising:
   an image processing device that reconstructs the tomographic image using the plurality of projection images.

8. The radiography system according to claim 1, wherein the correction marker includes a first correction marker that detects a deviation of a position of the focus in a left-right direction and a second correction marker that detects a deviation of the position of the focus in a direction intersecting the left-right direction.

9. An image processing device comprising:
   at least one processor,
   wherein the processor acquires a plurality of projection images obtained by tomosynthesis imaging from the radiography system according to claim 1 and derives a positional deviation amount of a focus of a radiation tube used for the tomosynthesis imaging on the basis of a position of a marker image included in the projection image and a reference position of the marker image.

10. The image processing device according to claim 9, wherein a tomographic image is reconstructed from the plurality of projection images on the basis of the positional deviation amount.

11. The image processing device according to claim 10, wherein the processor reconstructs a plurality of first tomographic images, in which a part of the object is included, from a plurality of projection images including a projection image obtained by projection at an irradiation position outside an overall imaging irradiation angle range among the plurality of projection images and reconstructs a plurality of second tomographic images, in which the entire object is included, from a plurality of projection images obtained by projection at irradiation positions inside the overall imaging irradiation angle range among the plurality of projection images, and the overall imaging irradiation angle range is an irradiation angle range in which an entire tomographic image including the entire object is obtainable in a case in which the tomographic image is reconstructed from the projection images obtained at each of the plurality of irradiation positions.

12. An image processing device comprising:
at least one processor,
wherein the processor acquires a plurality of projection images obtained by tomosynthesis imaging from the radiography system according to claim 1 and reconstructs a tomographic image from the plurality of projection images on the basis of a position of a marker image included in the projection image and a reference position of the marker image.

13. An image processing method executed by a computer, the image processing method comprising:
acquiring a plurality of projection images obtained by tomosynthesis imaging from the radiography system according to claim 1; and
deriving a positional deviation amount of a focus of a radiation tube used for the tomosynthesis imaging on the basis of a position of a marker image included in a projection image which is included in the acquired plurality of projection images and a reference position of the marker image.

14. An image processing method executed by a computer, the image processing method comprising:
acquiring a plurality of projection images obtained by tomosynthesis imaging from the radiography system according to claim 1; and
reconstructing a tomographic image from the plurality of projection images on the basis of a position of a marker image included in a projection image which is included in the acquired plurality of projection images and a reference position of the marker image.

15. A non-transitory computer-readable storage medium storing an image processing program that causes a computer to perform a process comprising:
acquiring a plurality of projection images obtained by tomosynthesis imaging from the radiography system according to claim 1; and
deriving a positional deviation amount of a focus of a radiation tube used for the tomosynthesis imaging on the basis of a position of a marker image included in a projection image which is included in the acquired plurality of projection images and a reference position of the marker image.

16. A non-transitory computer-readable storage medium storing an image processing program that causes a computer to perform a process comprising:
acquiring a plurality of projection images obtained by tomosynthesis imaging from the radiography system according to claim 1; and
reconstructing a tomographic image from the plurality of projection images on the basis of a position of a marker image included in a projection image which is included in the acquired plurality of projection images and a reference position of the marker image.

\* \* \* \* \*